United States Patent [19]

Cohen et al.

[11] 3,994,930

[45] Nov. 30, 1976

[54] 6-(3-CYANOPROPYL)-2-VINYL TETRAHYDROPYRAN-2-OL AND ITS TAUTOMER

[75] Inventors: Noal Cohen, Montclair; Michael Rosenberger, Caldwell; Gabriel Saucy, Essex Falls, all of N.J.

[73] Assignee: Hoffmann-La Roche Inc., Nutley, N.J.

[22] Filed: Sept. 15, 1975

[21] Appl. No.: 613,675

Related U.S. Application Data

[60] Continuation-in-part of Ser. No. 450,691, March 13, 1974, abandoned, which is a division of Ser. No. 67,296, Aug. 26, 1970, Pat. No. 3,813,417.

[52] U.S. Cl............................ 260/345.9; 260/345.2; 260/340.5; 260/464; 260/465.6; 260/465.8 R; 260/586 E
[51] Int. Cl.$^2$................ C07D 309/22; C07C 121/34
[58] Field of Search............ 260/345.9, 465.9, 465.6

[56] References Cited

UNITED STATES PATENTS

| | | | |
|---|---|---|---|
| 2,855,397 | 10/1958 | Ramsden | 260/345.9 |
| 3,478,106 | 11/1969 | Hughes et al. | 260/345.9 |
| 3,700,661 | 10/1972 | Saucy et al. | 260/345.9 |
| 3,816,458 | 6/1974 | Saucy | 260/340.9 |

OTHER PUBLICATIONS

Kharasch et al., "Grignard Reactions of Non-Metallic Substances", Prentice Hall, N. Y., pp. 575, 769, 1204 (1954).

*Primary Examiner*—James O. Thomas, Jr.
*Assistant Examiner*—Nicky Chan
*Attorney, Agent, or Firm*—Samuel L. Welt; George M. Gould; Raymond R. Wittekind

[57] ABSTRACT

A multi-step, stereospecific total synthesis of steroids utilizing intermediates having a cyanoalkyl A-ring precursor is disclosed. The initial starting materials for this process are the relatively inexpensive and commercially available reagents γ-butyrolactone and sodium cyanide. The process is suitable for the preparation of racemic or optically active, medicinally valuable steroids, particularly 19-norsteroids. It is a feature of this process that conditions employed during the multiple step synthesis are selected so as to retain the normally labile nitrile group even during hydrogenation and hydrolysis steps. In this manner, it is possible to employ the nitrile group as an A-ring precursor without resorting the protective groups as was heretofore found necessary in previous steroid total synthesis processes.

1 Claim, No Drawings

6-(3-CYANOPROPYL)-2-VINYL TETRAHYDROPYRAN-2-OL AND ITS TAUTOMER

This application is a continuation-in-part of copending U.S. patent application Ser. No. 450,691, filed Mar. 13, 1974, now abandoned, which in turn is a divisional of U.S. patent application Ser. No. 67,296, filed Aug. 26, 1970, now U.S. Pat. No. 3,813,417, issued May 28, 1974.

BRIEF DESCRIPTION OF THE INVENTION

The present invention relates to a multi-step, stereospecific total synthesis of racemic or optically active, medicinally valuable steroids utilizing a cyanoalkyl A-ring precursor. This synthesis is particularly adapted to produce 19-norsteroids.

One aspect of the present invention involves the preparation of racemic or optically active compounds of the following formula:

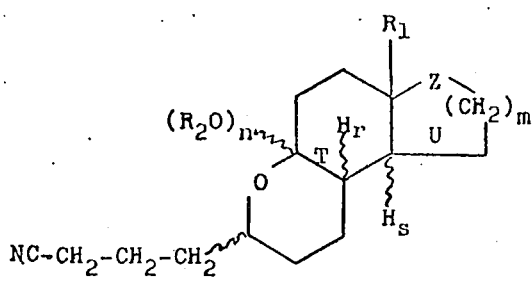

wherein $R_1$ is a primary alkyl group of from 1 to 5 carbon atoms; $R_2$ is hydrogen, lower primary alkyl or acyl; Z is carbonyl or a group of the formula

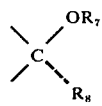

where $R_7$ is hydrogen, lower acyl, lower alkyl, aryl lower alkyl or tetrahydropyran-2yl; $R_8$ is hydrogen or lower aliphatic hydrocarbyl; T is either a single or double bond, U is a single or double bond and is a single bond when T is a single bond; m is 1 or 2; n is 0 or 1 and is 0 when T is a double bond and is 1 when T is a single bond; r is 0 or 1 and is 0 when T is a double bond and 1 when T is a single bond; and S is 0 or 1 and is 0 when U is a double bond and 1 when U is a single bond.

As used throughout the specification and appended claims, the term "hydrocarbyl group" denotes a monovalent substituent consisting solely of carbon and hydrogen and having from 1 to 20 carbon atoms; the term "aliphatic" with reference to hydrocarbyl groups, denotes groups containing no aromatic unsaturation, but which can be saturated or unsaturated, i.e., an alkyl, alkenyl or alkynyl group; the term "alkyl group" denotes a saturated hydrocarbyl group with a straight or branched chain having 1 to 20 carbon atoms; the term "alkenyl" denotes a straight or branched chain hydrocarbyl group having at least one olefinic bond and containing from 1 to 20 carbon atoms; the term "alkynyl group" denotes a straight or branched chain hydrocarbyl group containing at least one acetylenic bond having from 1 to 20 carbon atoms; the term "primary alkyl group" denotes an alkyl group having its valence from a carbon bonded to at least two hydrogens; the term "acyl group" denotes a group consisting of the residue of a hydrocarbyl monocarboxylic acid having 1 to 18 carbon atoms formed by removal of the hydroxyl portion of the carboxyl group; and the term "lower", as applied to any of the foregoing groups, denotes a group having a carbon skeleton containing up to and including 8 carbon atoms, such as methyl, ethyl, butyl, tertiary butyl, hexyl, 2-ethylhexyl, vinyl butenyl, hexenyl, ethynyl, ethylene, methylene, formyl, acetyl, 2-phenylethyl, and the like.

In the formulae presented herein, the various substituents on cyclic compounds are joined to the cyclic nucleus by one of three notations, a solid line — indicating a substituent which is in the β-orientation, (i.e., above the plane of the paper), a dotted line ---- indicating a substituent which is in the α-orientation (below the plane of the paper) or a wavy line—indicating a substituent which may be either the α- or β-orientation. The position of $R_1$ has been arbitrarily indicated as the β-orientation, although the products obtained in the examples are all racemic compounds unless otherwise specified. Preferred compounds are those wherein $R_1$ is n-alkyl, especially methyl and ethyl; m is 1 and, when s has a value of 1, the 9a- (when m is 1) or 10a- (when m is 2) hydrogen is trans-oriented with respect to $R_1$.

Subgeneric to the tricyclic compounds of formula I are the "dienes" having the formula:

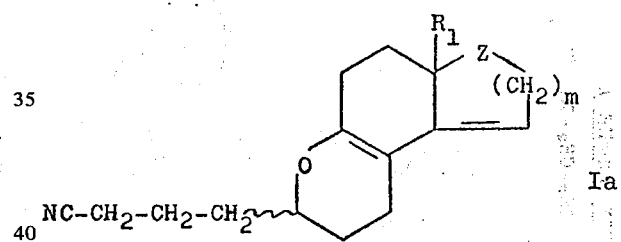

where $R_1$, m and Z are as above;

The "monoenes", represented by the formula

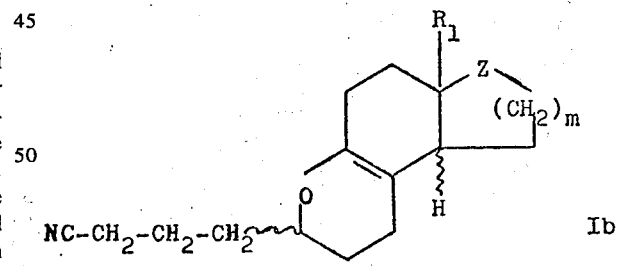

where $R_1$, m and Z are as above; and

The "perhydro" compounds represented by the formula:

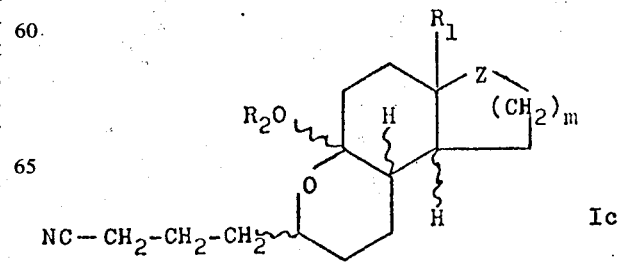

where $R_1$, $R_2$, m and Z are as above.

A further aspect of the present invention relates to processes useful in the preparation of compounds of formula Ia, utilizing commercially available and relatively inexpensive starting materials. For example, a preferred synthesis route for the preparation of compounds of formula Ia, utilizes 2,2-di-(3-cyanopropyl)-1,3-dioxolane as starting material. The latter compound is a known chemical which may be prepared in a manner known per se from δ-butyrolactone utilizing sodium cyanide as the source of the cyano groups. It is within the scope of the processes of the present invention to prepare either racemic or optically active forms of compounds of formula Ia. Such processes are summarized in the following reaction scheme:

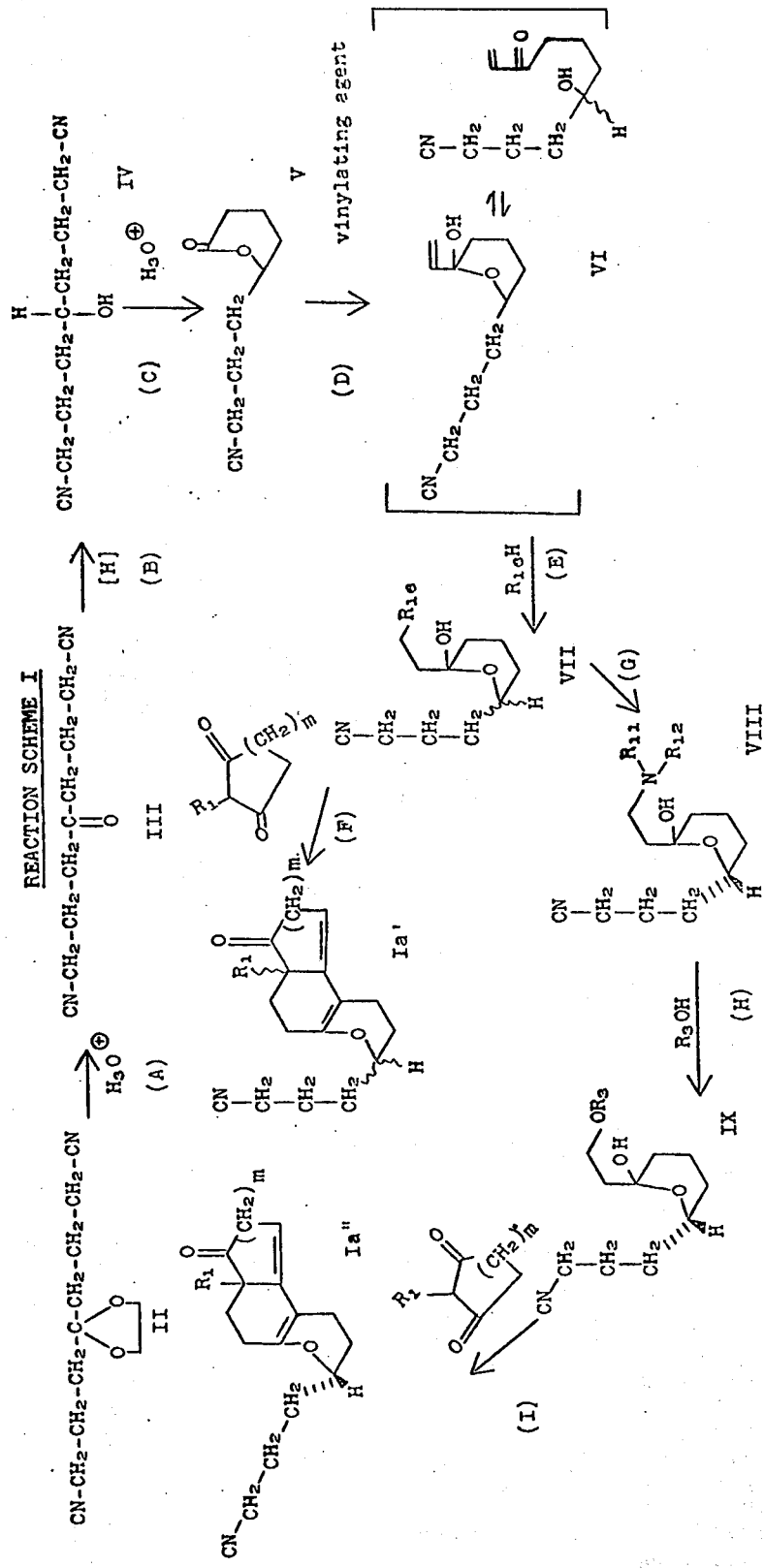

where $R_1$, and $m$ are as above; $R_3$ is hydrogen or lower alkyl; $R_{11}$ and $R_{12}$ independently are hydrogen and lower hydrocarbyl and $R_{16}$ is a hydrogen selected from the group consisting of chloro, bromo or iodo; hydroxy; lower alkoxy; lower hydrocarbylamino or di(lowerhydrocarbyl)amino.

In Step A the known compound 2,2-di(3-cyanopropyl)-1,3-dioxolane was selectively hydrolyzed utilizing dilute aqueous acid in the presence of a water-miscible organic solvent to yield 5-oxoazeleonitrile (III). Conditions for this hydrolysis are selected so as to retain the normally labile nitrile groups. Reduction of the carbonyl function in compound III is accomplished in Step B utilizing a metal hydride reducing agent, e.g., sodium borohydride to produce 5-hydroxyazeleonitrile (IV).

CHART FOR REACTION SCHEME 1

| Step | Reagents Operable | Reagents Preferred | Solvent Operable | Solvent Preferred | Conditions Operable | Conditions Preferred | Remarks |
|------|-------------------|--------------------|--------------------|-------------------|----------------------|----------------------|---------|
| A | dilute aqueous mineral acid; e.g., hydrochloric acid; dilute aqueous organic acid, e.g., acetic acid | dilute aqueous hydrochloric acid | a water miscible organic solvent selected from the group consisting of ketones, e.g., acetone; ethers, e.g., tetrahydrofuran and organic acids, e.g., acetic acid | acetone | −20 to +50° | 10 to 30° | |
| B | alkali metal borohydrides, e.g., sodium borohydride; alkoxy substituted alkali metal borohydrides, e.g., trimethoxysodium borohydride; alkoxy substituted complex metal hydride, e.g., lithium aluminum tri-t-butoxy hydride. | sodium borohydride | a non-ketonic organic solvent selected from the group consisting of lower alkanols, e.g., methanol; water miscible ethers, e.g., tetrahydrofuran; pyridine and dimethylformamide; or a mixture of water and one or more of the above. | aqueous methanol | −20° to boiling point of solvent | 10° to 30° | |
| C | one equivalent each of water and an acid selected from the group consisting of mineral acids, e.g. sulfuric acid, and organic sulfonic acids, e.g. p-toluenesulfonic acid | one equivalent of p-toluenesulfonic acid monohydrate or one equivalent each of water and sulfuric acid. | hydrocarbons, e.g. toluene, ethers, e.g. tetrahydrofuran; dimethylformamide. | toluene | 20° to 150° | 80° to 120° | |
| D | vinyl magnesium halides, e.g. vinyl magnesium chloride; vinyl alkali metals, e.g., vinyl lithium | vinyl magnesium chloride | ethers, e.g. diethyl ether, tetrahydrofuran | tetrahydrofuran | −20° to −100° | −40° to −70° | Product VI is not isolated. |
| E | hydrohalic acids, e.g. hydrochloric acid; lower alkanols, e.g. methanol; water; mono lower hydrocarbyl amines, e.g. α-methylbenzylamine; di(lower hydrocarbyl)amines. e.g. diethylamine. | for racemic series - diethylamine; for optically active series d- or l-α-methylbenzylamine. | where solubility permits, the reagent employed, e.g. methanol; hydrocarbons, e.g. benzene; ethers, e.g. tetrahydrofuran. | tetrahydrofuran | 0° to 50° | 10° to 30° | |
| F | 2-alkylcyclopentan-1,3-diones; 2-alkylcyclohexan-1,3-diones. | 2-methylcyclopentan-1,3-dione; 2-ethylcyclopentan-1,3-dione | hydrocarbons, e.g. toluene; ethers, e.g. tetrahydrofuran; dimethylformamide; dimethylsulfoxide. | toluene | 20° to 150° | 80° to 120° | An acidic or basic catalyst can be used, preferably a lower alkanoic acid, e.g. acetic acid. |
| G | a non-optically active acid selected from the group consisting of mineral acids, e.g. hydrochloric acid; hydrocarbylmonocarboxylic acids, e.g. acetic acid, hydrocarbyl dicarboxylic acids, e.g. oxalic acid. | oxalic acid | ketones e.g. acetone; lower alkanols, e.g. methanol; ethers, e.g. diethyl ether; hydrocarbons, e.g. benzene; nitriles, e.g. acetonitrile. | acetone, acetonitrile | −10° to 120° | 20° to 80° | |
| H | a. water; lower alkanols, e.g. methanol; b. lower hydrocarbyl or aromatic aldehydes, e.g. benzaldehyde. | a. methanol b. benzaldehyde | lower alkanols, e.g. methanol; hydrocarbons, e.g. toluene; ethers, e.g. tetrahydrofuran. | methanol | 20° to 120° | 40° to 60° | a catalytic amount of an inorganic base, preferably alkali metal carbonate or bicarbonate, e.g. sodium bicarbonate may be employed. |
| I | 2-alkylcyclopentan-1,3-diones; 2-alkylcyclohexan-1,3-diones | 2-methylcyclopentan-1,3-dione; 2-ethylcyclopentan-1,3-dione. | hydrocarbons, e.g. toluene; ethers, e.g. tetrahydrofuran; dimethylformamide; dimethylsulfoxide. | toluene | 20° to 150° | 80° to 120° | an acidic or basic catalyst can be used, preferably a lower alkanoic acid, e.g. acetic acid |

The symmetrical di-cyano alcohol produced above (IV) is then subjected to a selective acid hydrolysis procedure in Step C so as to produce 8-cyano-5-hydroxy-octanoic acid lactone. For this reaction it is necessary to employ one equivalent of water and one equivalent of strong acid, such as a mineral acid or an organic sulfonic acid such as p-toluene sulfonic acid. By utilizing one equivalent each of these reagents, it is possible to selectively hydrolyze only one of the two equivalent cyano moieties in compound IV.

It is likely that this reaction proceeds through the intermediate

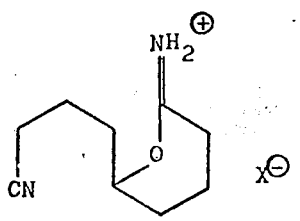

which is hydrolyzed by the water present to V.

In Step D the lactone of formula V is treated with a vinylating agent such as vinyl Grignard to produce a tautomeric mixture of 6-(3-cyanopropyl)-2-vinyl-tetrahydropyran-2-ol (which is named as a matter of convenience as a closed form). That a tautomeric mixture of 6-(3-propyl)-2-vinyl-tetrahydropyran-2-ol and the corresponding tautomer is formed in Step D is shown by ultraviolet and nuclear magnetic resonance spectroscopy. The diminished extinction coefficient at $\tau$ max 210 nm in the ultraviolet spectrum and the chemical shifts, multiplicity and band integrals of the protons of the reaction product of Step D evince the presence of both the open — and closed forms, i.e., the tautomeric mixture. See Example 50. This reaction is highly selective in that the reactive nitrile group is not affected by the vinylating agent under the carefully controlled reaction conditions.

Because of the susceptibility of the vinyl group of the compound of formula VI to polymerization, it is highly desirable to convert this compound without isolation to a more stable variant in Step E so as to produce a compound of formula VII. This is accomplished by treating the compound of formula VI with either water, an indicated hydrogen halide, a lower alkanol or a primary or secondary amine.

When it is desired to ultimately produce a racemic compound from this process scheme, it is possible to utilize any of the aforementioned reactants in process Step E, although a reactant of greatest preference is a di(lower hydrocarbyl)amine, preferably a di(lower alkyl)amine such as diethyl amine. In a final process step for the production of a racemic compound of formula Ia', the compound of formula VII is reacted in process Step F with a 2-alkyl-cyclopentan-1,3-dione or a 2-alkyl-cyclohexan-1,3-dione.

Where it is desirable to produce optically active benzopyrans it is necessary to employ in Step E an optically active primary or secondary amine so as to produce a compound of formula VII which is substituted with such an optically active amino group. Suitable optically active amine for this purpose include a α-methyl-benzylamine (also known as α-phenethylamine), dehydroabietylamine or desoxyephedrine.

When compound VIII contains an optically active amino moiety as $R_{16}$, it can be conveniently resolved in Step G to compound VIII. This resolution is conveniently effected by recrystallization of compound VII or, more effectively, by the recrystallization of a suitable crystalline acid addition salt of compound VII. Suitable acids include mineral acids, non-optically active hydrocarbyl monocarboxylic acids or hydrocarbyl dicarboxylic acids. Especially preferable is oxalic acid. The recrystallized acid addition salt is then decomposed by methods known per se to afford the resolved amine VIII.

Compound VIII can be converted to compound Ia'' by the method shown in Step F for the conversion of compound VII to compound Ia'. It is preferable when dealing with optically active amines such as compound VIII, to first convert them to the corresponding ether (IX) as shown in Step H. This is done by reaction of compound VIII with an excess of a lower alkanol, preferably methanol, and a lower hydrocarbyl or aromatic aldehyde, preferably benzaldehyde, in the presence of a catalytic amount of a weak inorganic base, preferably sodium bicarbonate. In this manner, the valuable optically active amine is trapped as its reaction product with the aldehyde, and can be recycled for future use.

Conversion of compound IX to compound Ia'' as shown in Step I is accomplished according to the identical procedure of Step F.

The condensation of vinyl ketone addition products such as VII, VIII or IX with a 2-alkyl cycloalkane 1,3-dione is one of the key features of this reaction. It is in this condensation that specific stereochemical induction at one member of the critical C/D-ring junction of the eventual steroidal product occurs. Thus, this invention is particularly advantageous in that it involves a unique asymmetric induction. The products of the condensation, i.e., the dienol ethers of formula Ia' and Ia'', have two asymmetric centers at positions 3 and 6a respectively, and, therefore, two racemates or four optical antipodes are possible. However, as a result of the condensation of this invention, when using a racemic starting material of formula VII, mainly one of the two possible racemates of formula Ia' is formed. For synthesis of a racemic steroidal final product, both of the racemates can be used. When using the optically active starting material of formulas VIII and IX, mainly a single optical antipode of formula Ia'' results. The specificity is increased by using compounds of formula IX rather than those of VIII and the desired optical antipode can be obtained in high purity by recrystallization of the crude reaction product. This is another reason for the inclusion of the additional Step H in the Reaction sequence. It has been found that when starting with a compound of formula VIII or IX with a 6-R-stereo-configuration, there is obtained the more desirable optical antipode of formula Ia'' having a 6aS(-6aβ)-stereo-configuration. Thus, to prepare steroidal materials having the more desirable 13β-stereo-configuration by the synthesis of this invention, one can start with the antipode of formula Ia'' which is prepared from antipode VIII or IX which are in turn prepared by resolution of the racemic amine VII. The unique asymmetric induction concurrent to the condensation of this invention renders the obtention of a single optical antipode as an end-product more facile. The simultaneous formation of the dienol ether of formula Ia'' with a unique asymmetric induction is a special advantage of this invention.

The keto dienes of formula Ia-1

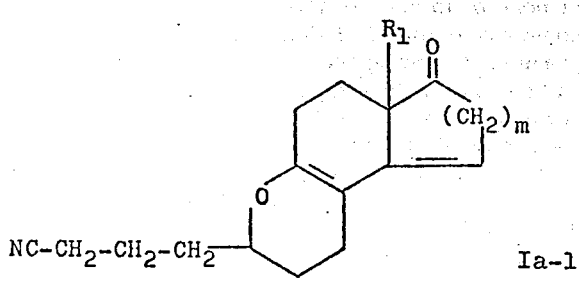

Ia-1 where $R_1$ and $m$ are as previously defined, are readily converted to the corresponding 7β-alcohols and their esters and ethers as represented by the formula Ia-2

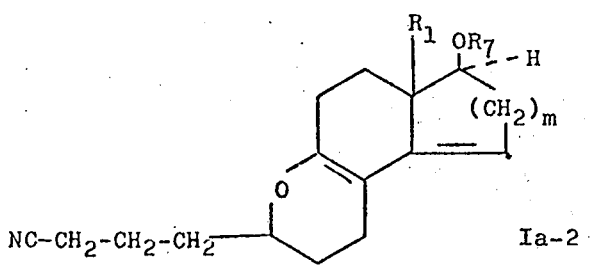

Ia-2 where $R_1$, $R_7$ and $m$ are as previously defined, by the sequence of reactions comprising reduction of the ketone to the alcohol and, if desired, subsequent esterification or etherification.

It is imperative that the reducing agent and the reaction conditions be chosen such that only the desired 7-ketone and not the cyano group on the side chain is reduced. The reduction can be effected by the use of a metal hydride reducing agent. The use of an alkaline metal borohydride, e.g. sodium borohydride; an alkoxy substituted alkaline metal borohydride, e.g. trimethoxysodium borohydride; or an alkoxy substituted complex metal hydride, e.g. lithium aluminum tri-t-butoxy hyride is preferred.

This reaction is effected in any suitable reaction medium, such as ethers, e.g. diethyl ether or tetrahydrofuran; water; a lower alkanol, e.g., methanol; N,N-di-(lower alkyl)-lower alkanoyl amides, e.g. N,N-dimethylformamide or aromatic amines, e.g. pyridine. The use of a hydrocarbon co-solvent, e.g. benzene, to solubilize the reactants is sometimes necessary.

The remaining reaction conditions are not narrowly critical, although it is generally preferred to effect the reduction at reduced temperatures, i.e., below about room temperature. Temperatures in the range of from about 0° C to about room temperature are normally employed.

The free alcohol is recovered from the reaction mixture after treatment of the mixture with acid. The alcohol can be esterified in known manner, for example, by base-catalyzed reaction with a carboxylic acid halide or carboxylic acid anhydride. Illustrative bases include inorganic bases such as sodium hydroxide and potassium hydroxide and organic bases such as a sodium alkoxide or an amine, especially a tertiary amine, and more particularly, pyridine and picoline.

The alcohol can also be etherified in a known manner by acid catalyzed reaction with an olefin such as isobutylene or 2,3-dihydropyran. Suitable acids include mineral acids, organic sulfonic acids and Lewis acids.

The keto dienes of formula Ia-1 can also be converted to their 7β-hydroxy-7α-hydrocarbyl derivatives represented by the formula Ia-3.

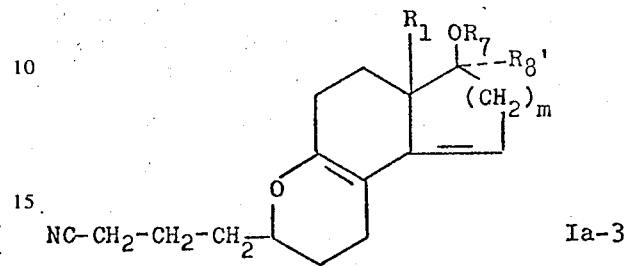

Ia-3 where $R_1$, $R_7$ and $m$ are as previously defined and $R_8'$ is lower hydrocarbyl,
by reaction of the keto diene with a hydrocarbyl magnesium halide such as methyl magnesium chloride or vinyl magnesium chloride, or a hydrocarbyl alkali metal compound such as methyl lithium, sodium acetylide, potassiium acetylide, and the like.

It should be noted that where an alkenyl or alkynyl group is introduced into the molecule at this time, it will be reduced to the corresponding alkyl group by the later hydrogenation steps of the present process.

It is well known that hydrocarbyl magnesium halides and hydrocarbyl alkali metal compounds readily add to nitrile moieties such as that present in the side chain of compound Ia-1. Surprisingly, it has been found that selective addition to the 7-keto function can be accomplished by carrying out the reaction under carefully controlled conditions. The reaction is run in an ethereal medium, e.g. ethyl ether or tetrahydrofuran, and in the case of alkynyl alkali metal, it is especially convenient to perform the reaction in liquid ammonia. The temperature of the reaction is kept between −50° and +50°, preferably, between −20° and +10°. The resulting reaction product is hydrolyzed to produce the free alcohol, which can be esterified as discussed above.

The next step of the general synthesis of the tricyclic compounds of this invention, comprises conversion of the diene of formula Ia to the monoene of formula Ib by catalytic hydrogenation. Suitable catalysts include the noble metals, such as platinum, palladium, rhodium, and the like, as well as Raney nickel, and other hydrogenation catalysts. These catalysts can be employed in the form of the metal alone or can be deposited on suitable support materials, such as carbon, alumina, calcium carbonate, barium sulfate, and the like. Palladium and rhodium are preferred as catalysts. The hydrogenation is preferably conducted in the presence of inert solvents, such as hydrocarbons, alcohols, ethers, and the like. The reaction conditions of pressure and temperature are not narrowly critical, and normally a hydrogen pressure of about 1 atmosphere and a temperature of about room temperature are employed. These ambient conditions are generally preferred to avoid significant hydrogenation of the 4a,9b(10b)-double bond and the labile nitrile group of the side chain, although more severe conditions, for example up to about 100° and up to about 10 atmospheres, can be employed if desired. The hydrogenation medium can be acidic, neutral, or basic, as may be desired, although a hydrocarbon medium, e.g. toluene or hexane, containing a tertiary amine, e.g. triethylamine, is preferred for best results. It is not advisable to combine a high reaction temperature with a strongly acidic or basic reaction medium as significant hydroylsis of the labile nitrile group may occur. In the case of hydrogenation of compounds of formula Ia-2 where $R_8$ is an unsaturated hydrocarbyl radical, the reaction, in addition to hydrogenating the ring double bond, also hydrogenates the 7α-hydrocarbyl substituent, converting it to an alkyl group.

Via the aforesaid catalytic hydrogenation C/D-trans compounds are formed in a major proportion when hydrogenating a diene of formula Ia-2 or Ia-3. This method thus provides an advantageous synthesis of C/D-trans steroidal materials. When hydrogenating a diene of formula Ia-1, C/D-cis compounds are formed in a major proportion. This method thus provides an advantageous synthesis of C/D-cis steroidal materials. The products of hydrogenation of diene Ia-1 are shown as Ib-1,

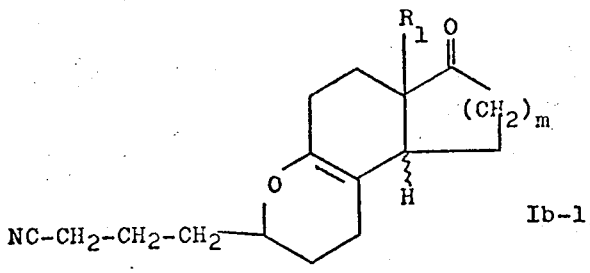

wherein $R_1$ and $m$ are as previously defined, and those from hydrogenation of dienes Ia-2 and Ia-3 are shown as Ib-2,

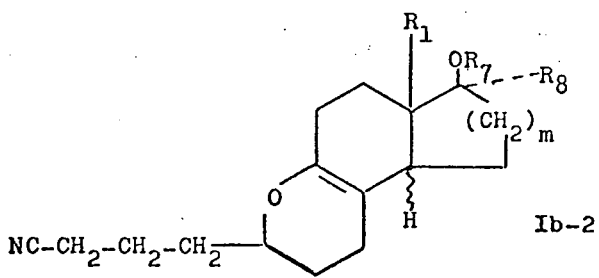

wherein $R_1$, $R_7$, $R_8$ and $m$ are as previously defined, Compounds of structure Ib-1 can be converted to those of formula Ib-2 by the identical techniques discussed above regarding the dienes of formula Ia.

When Z is carbonyl and the hydrogenation is effected under basic conditions, there is a tendency toward the production of predominantly 6a/9a(10a)-cis compounds; that is, the hydrogen atom in the 9a(10a)-position in formula Ib-1 is predominantly in the β- orientation. When these compounds are intended as intermediates for the synthesis of steroids having the C/D-trans-orientation, this technique is not particularly desirable. Although the ratio of β to α-orientation is about 1:1 at neutral conditions when hydrogenating a compound wherein Z is carbonyl, it is preferred to hydrogenate a 7β-alcohol or ester of formula Ia-2 or Ia-3 because the products of this hydrogenation are predominantly the 6a/9a(10a)-trans-compounds.

When monoenes of formula Ib-1 having C/D-trans-configuration are desired, it is preferable to first reduce the dienone of formula Ia-1 to a corresponding hydroxy compound of formula Ia-2 prior to the catalytic hydrogenation. Following the catalytic hydrogenation, the carbonyl moiety in formula Ib-1 can be regenerated by conventional means, such as oxidation with chromium trioxide or silver carbonate.

The monoene compounds of formula Ib prepared by the above described hydrogenation contain at least 3 asymmetric centers, at positions 3, 6a and 9a when $m$ is 1 and at positions 3, 6a and 10a when $m$ is 2. With respect to these three centers, there are thus eight stereoisometric configurations possible. By virtue of the unique asymmetric induction of this invention, proceeding from a racemic starting material of formula VII only four of the stereoisomers of formula Ib are prepared, and proceeding from an optically active starting material of formula VIII or IX only two of the stereoisomers of formula Ib are prepared. Moreover, by the above-described hydrogenation of this invention and by appropriate selection of the 7-substituents in the diene of formula Ia subjected to the hydrogenation, there can predominantly be prepared the desired 6a, 9a(10a)-trans-stereo-configuration. Thus, the eventual obtention of the more desired 13β-C/D-trans-configuration in the ultimate steroidal product is rendered more facile by the stereo-selective reactions provided by this invention.

Illustrative examples of the monoene of formula Ib include:

3-(3-cyanopropyl)-6a-methyl-2,3,5,6,6a,8,9,9a-octahydrocyclopenta[f][1]benzopyran-7(1H)-one, 3-(3-cyanopropyl)-6a-methyl-1,2,3,5,6,6a,7,8,9,9a-decahydrocyclopenta[f][1]benzopyran-7β-ol, 3-(3-cyanopropyl)-6a-ethyl-2,3,5,6,6a,8,9,9a-octahydro cyclopenta[f][1]benzopyran-7(1H)-one, 3-(3-cyanopropyl)-6a-ethyl-1,2,3,5,6,6a,7,8,9,9a-decahydrocyclopenta[f][1]benzopyran-7β-ol, 3-(3-cyanopropyl)-6a-methyl-1,2,3,5,6,6a,8,9,10,-10a-decahydro-naphtho[2,1,-b]pyran-7-one, 3-(3-cyanopropyl)-6a-methyl-1,2,5,6,6a,8,9,10,10a-decahydro-3H-naphtho[2,1-b]pyran-7β-ol, 3-(3-cyanopropyl)-6a-ethyl-1,2,3,5,6,6a,7,8,9,10,-10a-decahydro-naphtho [2,1-b]pyran-7-one, 3-(3-cyanopropyl)-6a-ethyl-1,2,5,6,6a,8,9,10,10a-decahydro-3H-naphtho[2,1-b]pyran-7β-ol.

The next reaction of applicants' general process for the compounds of this invention is the conversion of the monoene of formula Ib of the perhydro compound of formula Ic by the reaction of the monoene with a compound having the formula:

$$R_2OH \qquad \qquad X$$

wherein $R_2$ is as previously defined.

That is, the monoene of formula Ib is reacted with water, a primary alcohol, or a carboxylic acid. This reaction is catalyzed by mineral or organic acids, for example, hydrochloric acid, phosphoric acid, sulfuric acid, para-toluene sulfonic acid, and the like. Sulfuric acid is the preferred acid catalyst, and water, the preferred reactant. Although it is not necessary, it is desirable to conduct this reaction in the presence of an added solvent, particularly in the event the compound of formula X is water. In this case, it is desirable to employ a solvent which is both miscible with water and a solvent for the monoene of formula Ib. Solvents of this nature include acetone, tert-butyl alcohol, dioxane and the like. The reaction temperature is not critical, and ambient temperature is normally employed although higher and lower temperatures could be employed if desired.

As with the compounds of formulae Ia-1 and Ib-1, the compounds of the general formula Ic wherein Z is carbonyl

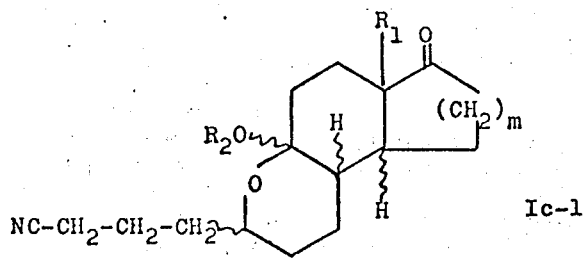

and $R_1$, $R_2$ and $m$ are as previously defined, are readily converted to their corresponding 7β-alcohol or esters Ic-2

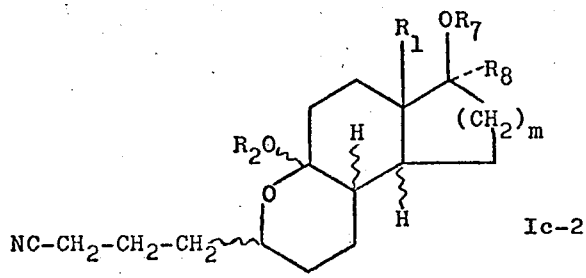

wherein $R_1$, $R_2$, $R_7$, $R_8$ and $m$ are as previously defined, by the previously described method.

In a modification of the general technique outlined above, one can simultaneously effect the hydrogenation and hydration steps, for example, by hydrogenation of a diene of formula Ia in aqueous sulfuric acid. When this simultaneous hydrogenation-hydration is effected, it is preferred to begin with a diene having a hydroxyl group in the 7β-position.

Illustrative examples of the compounds falling within the scope of formula Ic include:

3-(3-cyanopropyl)-6a-methyl-4a-hydroxyperhydrocyclopenta [f][1]benzopyran-7-one, 3-(3-cyanopropyl)-6a-methyl-4a-hydroxyperhydrocyclopenta [f][1]benzopyran-7β-ol, 3-(3-cyanopropyl)-6a-ethyl-4a-hydroxyperhydrocylcopenta [f][1]benzopyran-7-one, 3-(3-cyanopropyl)-6a-ethyl-4a-hydroxyperhydrocyclopenta [f][1]benzopyran-7β-ol, 3-(3-cyanopropyl)-6a-methyl-4a-hydroxyperhydro-3H-naphtho [2,1-b]pyran-7-one, 3-(3-cyanopropyl)-6a-methyl-4a,7β-dihydroxyperhydro-3H-naphtho[2,1-b]pyran, 3-(3-cyanopropyl)-6a-ethyl-4a-hydroxyperhydro-3H-naphtho [2,1-b]pyran-7-one, 3-(3-cyanopropyl)-6a-ethyl-4a,7β-dihydroxyperhydro-3H-naphtho[2,1-b]pyran.

As indicated above, the tricyclic compounds of this invention are useful as intermediates for the preparation of various medicinally valuable steroid compounds. This is illustrated by the following Reaction Scheme.

REACTION SCHEME II

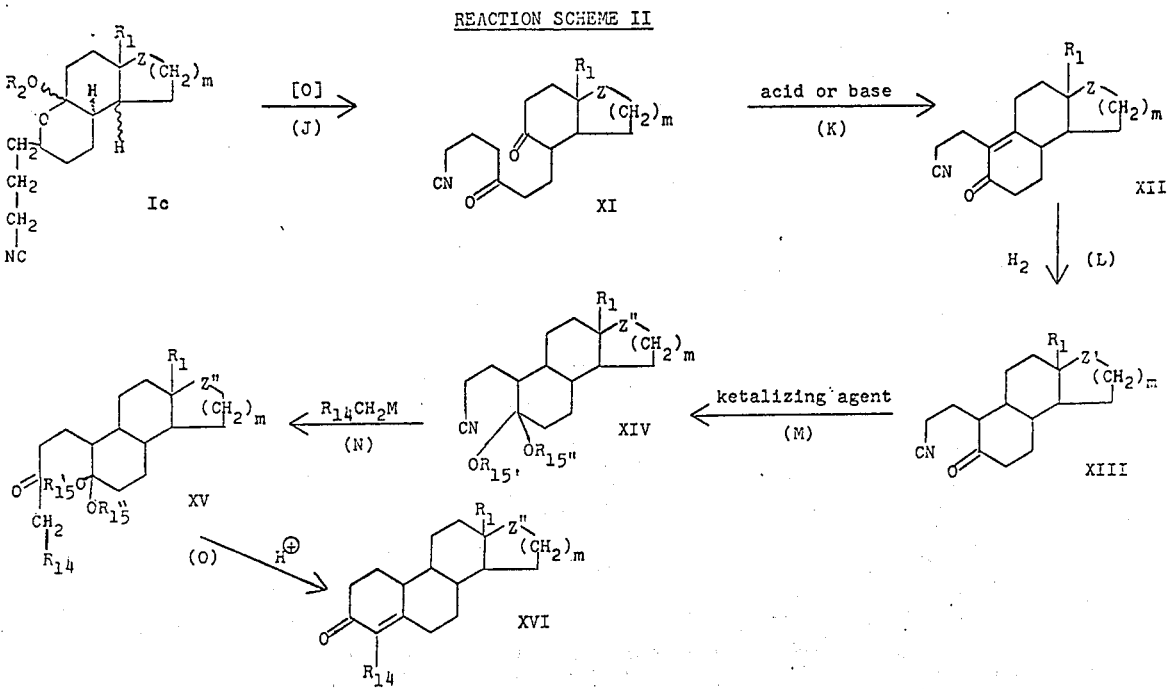

where $R_1$, $R_2$, Z and $m$ are as above; $Z'$ is carbonyl or a group of the formula

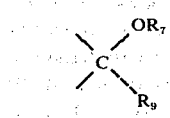

where $R_7$ is as defined above and $R_9$ is hydrogen or lower alkyl; $Z''$ is a group of the formula

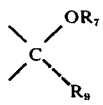

where $R_7$ and $R_9$ are as defined above, or a group of the formula

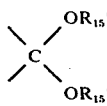

where $R_{15}'$ and $R_{15}''$ are each independently the same lower alkyl or taken together are lower alkylene having from 1 to 4 carbons; and $R_{14}$ is hydrogen, lower hydrocarbyl, aryl, or aryl lower alkyl.

In the first step of this reaction scheme (J), compounds of formula Ic are oxidized to form bicyclic compounds of the formula XI by contact with such oxidizing agents such as chromic acid, potassium dichromate, or potassium permanganate, Jones reagent (chromic acid, sulfuric acid and acetone), or a chromic acid-acetic acid mixture are preferred as oxidizing agents. The nature of Z is unchanged in this reaction, except where Z is hydroxy methylene [—CH(OH)—]. In this instance, unless the hydroxyl group is protected, as by formation of a lower acyl ester, it is oxidized to form a carbonyl group. One can then obtain a hydroxylated product by hydrolysis of the product ester. Because of the labile nature of the nitrile group on the side chain, care must be taken to control the reaction conditions, especially when using a strongly acidic oxidizing medium such as Jones reagent. It is preferred to effect hydration and oxidation in one step without isolating the intermediate hydration product.

In the second step (K) bicyclic compound XI is treated with acid or base to effect cyclization to XII. When acid is used as the catalyst, it is preferred that the water of reaction be removed, as by refluxing the reaction mixture with an azeotropic agent and separating the water from the condensate. It is preferred to effect

CHART FOR REACTION SCHEME II

| Step | Reagents Operable | Reagents Preferred | Solvents Operable | Solvents Preferred | Conditions Operable | Conditions Preferred | Remarks |
|---|---|---|---|---|---|---|---|
| J | chromic acid; alkali metal dichromates, e.g., potassium dichromate; alkali metal permanganate, e.g., potassium permanganate | chromic acid-sulfuric acid (Jones reagent) | ketones, e.g. acetone; ethers, e.g. diethyl ether; lower organic acids, e.g. acetic acid; pyridine; dimethylformamide; mixtures of the above with water | acetone, acetic acid | −20° to +100° | 0° to 30° | |
| K | mineral acids, e.g., sulfuric acid; organic sulfonic acids; e.g., para-toluenesulfonic acid; alkali metal hydroxides, e.g., sodium hydroxide | catalytic amount of sodium hydroxide | lower alkanols, e.g., methanol; hydrocarbons, e.g., toluene | methanol | 20° to 150° | 50° to 100° | For acid catalyzed reaction it is preferable to remove water of reaction by azeotropic distillation. |
| L | metal catalysts in presence of a mineral acid, an alkali, metal hydroxide or an organic amine | palladium-charcoal in the presence of an organic amine, e.g. triethylamine | lower alkanols, e.g., methanol; ethers, e.g., tetrahydrofuran; lower organic acids, e.g., acetic acid; hydrocarbons, e.g., benzene | tetrahydrofuran | 0° to 100° up to 10°atm | 20° to 30° 1 to 3atm | |
| M | a. lower alkanols, e.g. methanol; lower alkylene diols, e.g., ethylene glycol, 2,3-butanediol; b. catalytic amounts of either mineral acids, e.g. sulfuric acid; organic sulfonic acids, e.g. para-toluenesulfonic acid, or Lewis acids, e.g., borontrifluoride; c. tri(lower alkyl) orthoformates | a. ethylene glycol b. sulfuric acid c. trimethylorthoformate | ethers, e.g., tetrahydrofuran; hydrocarbons, e.g., toluene; lower alkanols, e.g., methanol | tetrahydrofuran | 0° to 100° | 20° to 50° | |
| N | organomagnesium halides, e.g., methylmagnesium chloride, organo alkali metal reagents, e.g., methyl lithium | methyl lithium | ethers, e.g., diethyl ether, tetrahydrofuran; hydrocarbons, e.g., hexane, toluene | diethyl ether or tetrahydrofuran | −50° to +50° | −10° to +10° | |
| O | dilute mineral acids, e.g., hydrochloric acid; organic sulfonic acids, e.g., para-toluenesulfonic acid | dilute hydrochloric acid | lower alkanols, e.g., methanol; ethers, e.g., tetrahydrofuran | methanol | 20° to 100° | 50° to 70° | | the cyclization by a base catalyzed dehydration using only a catalytic amount of a base, most preferably an alkali metal hydroxide. The use of only a small amount of base is critical to this reaction because of the base sensitive nature of the nitrile group.

The hydrogenation of cyclo-olefin XII to tricyclic compound XIII (L) is preferably effected with a noble metal catalyst, e.g. a palladium-charcoal catalyst or a rhodium catalyst. The reaction can be carried out either in a neutral, acidic, or basic medium and best results are obtained when the reaction is conducted in the presence of a base, preferably an organic amine. The other reaction conditions of temperature and pressure are chosen so that only the desired double bond is reduced and the potentially reducible nitrile group is left untouched. During this hydrogenation reaction, an alkenyl or alkynyl group substituted in the 7α-position of compound XII is reduced to the corresponding alkyl group.

Compound XIII is next reacted (M) with either a lower alkanol or lower alkylene diol in the presence of a strong acid and a tri(lower alkyl) orthoformate to afford a ketal of structure XIV. Where Z' in compound XV is a carbonyl group, it is also ketalized. When the ketalizing agent is a lower alkanol there may be formed in addition to compound XIV an enol ether of structure XVII.

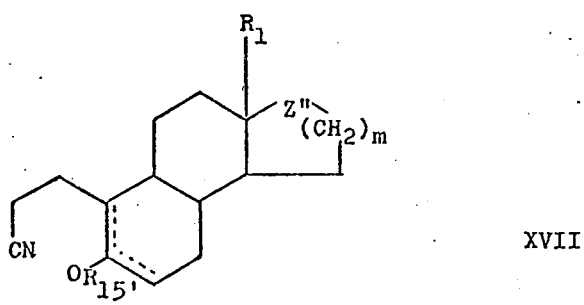

XVII where $R_1$, $R_{15}$, $Z''$ and $m$ are as above. Compounds of formula XIV and XVII need not be separated and can be carried through the remainder of the synthetic sequence as a mixture.

With all of the potential carbonyl groups of compound XIV protected as ketals or enol ethers, the nitrile group is reacted with an organo metallic reagent followed by an aqueous work-up as shown in Step N to afford a tricyclic ketone of structure XV. If, in compound XIV, $Z''$ is a group wherein $R_7$ is acyloxy, such a group will be converted to a hydroxy group by the reaction conditions of Step N. Reacylation of this hydroxy group can be effected at a later stage.

In a final step (O), the protective ketal groups of compound XV are removed and the resulting compound is cyclized to the steroid of structure XVI. This is conveniently done by treating compound XV with an aqueous acid, preferably a mineral acid or an organic sulfonic acid. Steroids of structure XVI are well known intermediates for the preparation of medicinally valuable steroids. See for example, D. Lednicer, Ed., "Contraception: The Chemical Control of Fertility", M. Dekka, Inc., New York, N.Y., 1969.

Compounds of formula XVI can be selectively alkynlated by suitable organometallic acetylides affording norgestrel (13β-ethyl-17α-ethynyl-17β-hydroxy-gon-4-en-3-one). Norgestrel is a potent clinically useful progestational agent utilized in combination with ethynylestradial as the therapeutically effective contraceptive, Orval (D. Lednicer, supra., pages 28 to 66 and 78. Exemplary of the suitable alkynylating agents to effect the conversion to norgestrel are the alkali acetylides such as lithium acetylide, potassium acetylide, sodium acetylide, etc.

The reaction is carried out in the presence of liquid ammonia in a suitable solvent such as for example, benzene or toluene. The alkynylation is effected preferably at reflux temperature of the reaction medium although temperatures from between −60° to −30° are suitable. Exemplary of other suitable reagents to effect the acetylenic addition are lithium acetylide-ethylene diamine complex in dimethylformamide solvent and Grignard analogs such as mono and bis acetylene magnesium halides. The acetylene addition, known with 13-methyl-substituted steroids, is similarly effected with a more bulky 13-ethyl-substituted steroids notwithstanding the increased steric hindrance in the latter configuration.

Compound of formula XVI wherein Z is carbonyl can be converted into corresponding pregnane compounds, i.e., compounds in which Z is of the formula

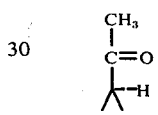

by known procedures. See for example, "Steroids", L. F. Fieser and M. Fieser, Rheinhold Publishing Corp., New York, N.Y., pages 544–545. Thus, for example, 19-nor-14β-andros-4-en-3,17-dione can be converted into 19-nor-14β,17α-progesterone and des-A-androst-9-en-5,17-dione can be converted into des-A-pregn-9-en-5-one. These procedures for converting androst-17-ones into pregnanes are best effected if all carbonyl groups other than that in the 17-position are initially protected.

An alternative synthesis for steroids of structure XVI from tricyclic compounds of structure Ia involving the intermediacy of known compounds of structure XVII is depicted in Reaction Scheme III. Compounds of structure XVII can be prepared from those of structure Ia by reaction with an organo metallic agent followed by an aqueous work-up as shown in Reaction Step P. This process is carried out in an identical manner to that shown in Reaction Step N from Reaction Scheme II. If one desires compounds of structure XVII where Z is a carbonyl group, it is advisable to first protect the carbonyl group in compound Ia-1 as a ketal by methods known per se and, after the completion of reaction Step P, the ketal can be hydrolyzed back to the carbonyl group. If one starts with compounds of structure Ia-2 or Ia-3, where $R_7$ is an acyl group, such a group will be hydrolyzed during the course of Reaction Step P to a hydroxy group. Such a hydroxy group can, if desired, be reacylated in the usual manner. Where, in compound XVII, Z contains an $R_8$ group which is alkenyl or alkynyl, such a group will be reduced to the corresponding alkyl group during the later conversion of compound XVII to steroids of the structure XVI.

REACTION SCHEME III

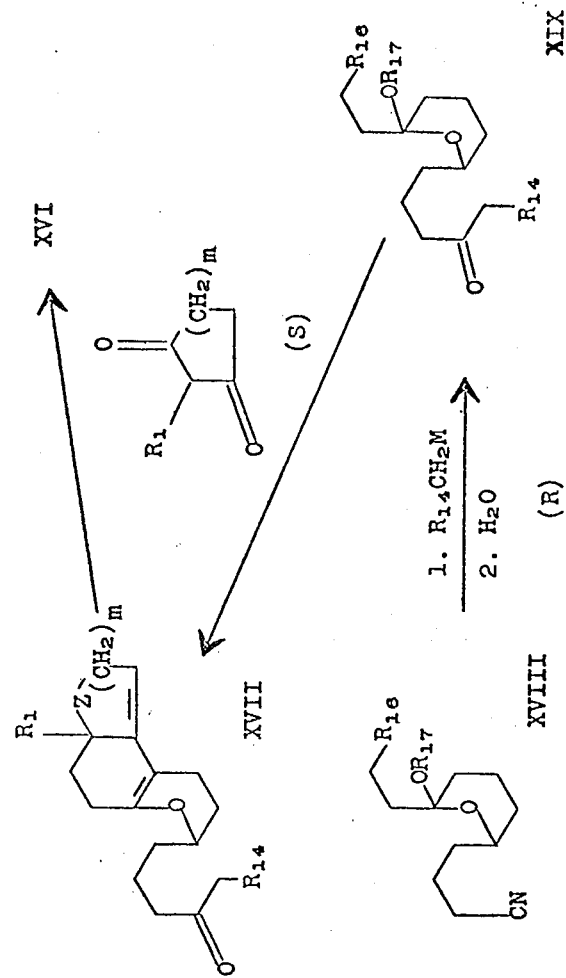

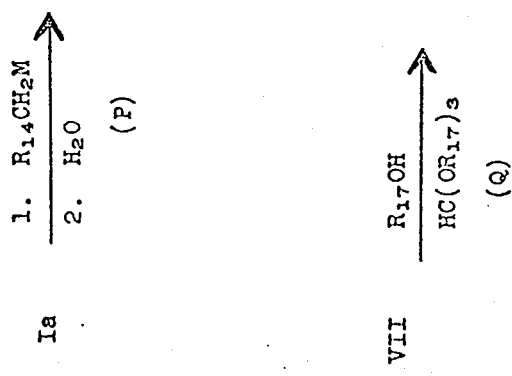

where $R_1$, $R_{14}$, $R_{16}$, Z and $m$ are as previously defined and $R_{17}$ is lower alkyl.

An alternative synthesis of compounds of structure XVII is depicted in Reaction Scheme III starting with compounds of structure VII. In the first step, Reaction Step Q, the hemiketal function of compound VII is protected as the ketal function by reaction with a lower alkanol and a tri(lower alkyl) orthoformate in the presence of a strong acid such as a Lewis acid, preferably boron trifluoride.

In the next step (R) compound XVIII is reacted with an organo metallic agent followed by an aqueous workup to afford a compound of structure XIX. This reaction is carried out in the same manner as that shown in Step N of Reaction Scheme II. The resulting ketone is then reacted in Step S with a 2-alkylcycloalkan-1,3-dione in a manner identical with that shown in Step F of Reaction Scheme I to afford compounds of structure XVII where Z is carbonyl.

In the claims, all compounds shall be construed to

CHART FOR REACTION SCHEME III

| | Reagents | | Solvent | | Conditions | | |
|---|---|---|---|---|---|---|---|
| Step | Operable | Preferred | Operable | Preferred | Operable | Preferred | Remarks |
| P | | | THE SAME AS IN STEP N | | | | |
| Q | a. lower alkanols, e.g. methanol | a. methanol | lower alkanols, e.g. methanol; ethers, e.g. tetrahydrofuran. | methanol | 0° to 100° | 20° to 30° | |
| | b. lower alkyl orthoformates, e.g. trimethylorthoformate | b. trimethylorthoformate | | | | | |
| | c. mineral acids, e.g. sulfuric acid; organic sulfonic acids, e.g. paratoluene-sulfonic acid; Lewis acids, e.g. boron trifluoride. | c. borontrifluoride | | | | | |
| R | | | THE SAME AS IN STEP N | | | | |
| S | | | THE SAME AS IN STEP F | | | | | include, independently, the racemic form of the compound and independently, each enantiomeric form, i.e. $d$ and $l$ configurations unless specifically indicated otherwise.

The following examples are illustrative. All temperatures are in degrees Centigrade and all products having centers of asymmetry are racemic unless specifically indicated otherwise.

EXAMPLE 1

A solution of 347.4 g. (1.67 moles) of 2,2-di-(3-cyanopropyl)-1,3-dioxolane in 1.5 l. of acetone was cooled to 10° and treated with 1 l. of a cold (10°) 3N aqueous hydrochloric acid solution. The mixture was allowed to stand at room temperature for 18 hours then concentrated to a volume of approximately 1.5 l. at 40° and aspirator pressure. The organic materials were extracted with methylene chloride (1 × 600 ml. and 3 × 300 ml.) and the combined organic extracts were washed with saturated brine (2 × 200 ml.) dried and concentrated at reduced pressure giving 276 g. of oily 5-oxoazeleonitrile.

A sample of this material on distillation yielded pure 5-oxoazeleonitrile, b.p. 137°–140°/0.05 mm., as a colorless liquid.

ir: $\nu_{max}^{CHCl_3}$ 2250 (C≡N) and 1710 (C=O) cm$^{-1}$.

Anal. calcd. for $C_9H_{12}N_2O$: C, 65.83; H, 7.37; N, 17.06. Found: C, 66.08; H, 7.46; N, 17.07.

EXAMPLE 2

A solution of 276 g. (1.67 moles) of crude 5-oxoazeleonitrile in 500 ml. of methanol and 500 ml. of water was added to a cooled (5°), stirred solution of 33 g. (0.873 mole) of sodium borohydride in 300 ml. of water. The temperature was held at 5°–10° during the addition. After addition was complete, the mixture was stirred at room temperature 90 minutes.

Dilute aqueous sulfuric acid solution (4N) was added to the reaction mixture with cooling (10°) until pH 2–3. The organic materials were extracted with methylene chloride (1 × 500 ml., 2 × 250 ml. and 2 × 125 ml.) The combined organic extracts were washed with brine (1 × 200 ml.) and dried. Removal of solvents at reduced pressure gave 272 g. (98%) of 5-hydroxyazeleonitrile as a colorless, mobile liquid.

A sample of this material on evaporative distillation gave an analytical specimen, b.p. 145°–175° (bath temp.)/0.01 mm.

ir: $\nu_{max}^{CHCl_3}$ 3625, 3500 (OH) and 2250 (C≡N) cm$^{-1}$.

Anal. calcd. for $C_9H_{14}N_2O$: C, 65.03; H, 8.49; N, 16.85; Found: C, 64.92; H, 8.35; N, 16.68.

EXAMPLE 3

A solution of 272 g. (1.64 moles) of crude 5-hydroxyazeleonitrile in 1.5 l. of toluene was treated with 312 g. (1.64 moles) of p-toluenesulphonic acid monohydrate and the mixture was stirred and refluxed for 1 hour. The starting materials dissolved and were replaced by a precipitate of ammonium tosylate which, after cooling was filtered off with suction and washed with fresh toluene (2 × 500 ml.).

The combined filtrate and washings were washed with water (3 × 100 ml.) dried and concentrated at reduced pressure. The residue on distillation furnished pure 8-cyano-5-hydroxyoctanoic acid lactone (214 g.; 78.2%), b.p. 162°–165°/0.2 mm.

ir: $\nu_{max}^{CHCl_3}$ 2250 (C≡N), 1730 and 1250 (δ-lactone) cm$^{-1}$.

Anal. calcd. for $C_9H_{13}NO_2$: C, 64.65; H, 7.84; N, 8.38; Found: C, 64,63; H, 7.89; N, 8.18.

Similar results were obtained when one mole equivalent of concentrated sulfuric acid and one mole equivalent water were substituted for the p-toluenesulphonic acid monohydrate.

EXAMPLE 4

A stirred solution of 8.35 g. (0.05 mole) of 8-cyano-5-hydroxyoctanoic acid lactone in 40 ml. of dry tetrahydrofuran (THF) was cooled to −70° and treated over 14 minutes wih 38 ml. (0.076 mole) of a solution of vinylmagnesium chloride in THF (2M). The mixture was then stirred for 6 minutes at −50°, cooled to −65° and decomposed with 2 ml. of methanol and subsequently with aqueous ammonium chloride solution (5%; 50 ml. — the cooling bath was removed for the last addition and the temperature rose to 10°). Sufficient acetic acid was added to yield two clear layers (pH still on basic side).

The organic layer was separated and the aqueous layer was extracted with THF (100 ml. and 2 × 50 ml.) and the combined THF solutions containing 6-(3-cyanopropyl)-2-vinyltetrahydropyran-2-ol were treated with 10 ml. of diethylamine and left at room temperature for 1.5–2 hours. Removal of solvents at reduced pressure yielded crude 2-(2-diethylaminoethyl)-6-(3-cyanopropyl)-tetrahydropyran-2-ol (17 g.) as an oil.

This material was treated with 50 ml. of 10% aqueous acetic acid and 20 ml. of ether. The aqueous layer was reextracted with 20 ml. of additional ether and the combined ether extracts were reextracted with 10% aqueous acetic acid (2 × 25 ml.) then discarded. The combined aqueous acid extracts was made alkaline with 10% aqueous sodium carbonate solution and the Mannich base was isolated by extraction with methylene chloride (5 × 20 ml.). Solvent removal at reduced pressure gave the pure 2-(2-diethylaminoethyl)-6-(3-cyanopropyl)-tetrahydropyran-2-ol (10.84 g.; 81%) as a mobile, pale-yellow oil.

ir: $\nu_{max}^{film}$ 3150, 3450 (bonded OH and NH), 2250 (C ≡ N), 1710 (weak C=O of open form).

Anal. calcd. for $C_{15}H_{28}N_2O_2$: C, 67.12; H, 10.52; N, 10.44; Found: C, 67.15; H, 10.37; N, 10.28.

EXAMPLE 5

A solution of 18.92 g. (0.0706 mole) of Mannich base from Example 4, 8.72 g. (0.0778 mole) of 2-methyl-1,3-cyclopentandione 64 ml. of glacial acetic acid and 253 ml. of toluene was stirred and refluxed for 1.5 hours. After cooling, the solution was washed twice with 100 ml. portions of water, once with 100 ml. of 0.5N aqueous HCl, twice with 100 ml. portions of saturated aqueous sodium bicarbonate, dried, filtered and concentrated at reduced pressure giving 16.3 g. (85.4%) of orange solid dienolether mixture which was essentially homogeneous on tlc analysis. Recrystallization from 20 ml. of ethanol gave 11.54 g. (60.4%) of pale orange crystals, m.p. 95°–99°. By further recrystallization of a sample from ethanol an analytical specimen of 3-(3-cyanopropyl)-6a-methyl-1,2,3,5,6,6a-hexahydrocyclopenta-[f][1]benzopyran-7(8H)-one was obtained as pale-yellow crystals, m.p. 100°–101.5°.

uv: $\lambda_{max}^{EtOH}$ 253 mμ (ε19500);

ir: $\nu_{max}^{CHCl_3}$ 2250 (C ≡ N), 1730 (C=O), 1630 (C=C) cm$^{-1}$;

nmr: $\delta_{TMS}^{CDCl_3}$ 5.47 (triplet, J=2 Hz, H—C=C, 1 proton), 3.85 (multiplet, H—C—O, 1 proton), 1.14 (singlet, C$_6$—CH$_3$, 3 protons) ppm; Mass spectrum m/e 271 (M$^+$).

Anal. calcd. for $C_{17}H_{21}NO_2$: C, 75.24; H, 7.80; N, 5.16; Found: C, 75.36; H, 7.75; N, 5.03.

EXAMPLE 6

A solution of 6 g. (0.0222 mole) of dienolether from Example 5 in 35 ml. of benzene was added dropwise, over a 10 minute period to an ice-cold solution of 0.864 g. (0.0228 mole) of sodium borohydride in 50 ml. of ethanol and 5 ml. of water. The resulting mixture was stirred with ice-bath cooling for 25 minutes then the cooling bath was removed and the mixture was stirred at ambient temperature for an additional 15 minutes. The mixture was poured into aqueous brine and the organic layer was separated. The aqueous layer was extracted twice with ether. The combined organic solutions were washed once with brine, dried and concentrated at reduced pressure giving 6 g. of yellow, solid 3-(3-cyanopropyl)-6a-methyl-1,2,3,5,6,6a,7,8-octahydrocyclopenta[f][1]benzopyran-7β-ol. TLC analysis showed a single spot and the absence of starting ketone.

ir: $\nu_{max}^{CHCl_3}$ 3450, 3600 (OH), 2250 (C ≡ N), 1640 (dienolether) cm$^{-1}$.

EXAMPLE 7

The above crude alcohol from Example 6 (6 g.) in 35 ml. of toluene and 25 ml. of tetrahydrofuran was hydrogenated over 1 g. of preequilibrated AK-4 5% palladium on carbon at room temperature and 1 atm. for 23 hours. A total of 543 ml. of hydrogen was consumed (555 ml. theory for 0.022 mole). The catalyst was filtered with suction on a pad of Celite and the filter cake was washed well with toluene. The combined filtrate and washes were concentrated at reduced pressure giving 6.65 g. of 6a,9a-trans-3-(3-cyanopropyl)-6a-methyl-1,2,3,5,6,6a,7,8,9,9a-decahydrocyclopenta[f][1]benzopyran-7β-ol as a pale-yellow foam.

ir: $\nu_{max}^{film}$ 3480 (OH), 1680 (enolether), 2250 (C ≡ N) cm$^{-1}$. The peak due to the dienolether at 1640 cm$^{-1}$ was completely absent.

EXAMPLE 8

The above crude enolether from Example 7 (6.65 g.) was dissolved in 165 ml. of acetone and treated with 15 ml. of 0.5N aqueous sulfuric acid solution. The resulting solution was stirred at room temperature for 3.5 hours. This solution containing 6a,9a-trans-3-(3-cyanopropyl)6a-methyl-perhydrocyclopenta[f][1] benzopyran-4a,7β-diol was then cooled using an ice-bath and treated with 16.5 ml. of Jones reagent (4N with respect to OH groups), dropwise, over 15 minutes. The ice-bath was removed and the resulting red mixture was stirred at room temperature for 3¼ hours. After decomposition of the excess oxidant with sodium bisulfite, the mixture was diluted with brine and benzene and the organic layer was separated. The aqueous layer was extracted three times with benzene and once with ether. The combined organic solutions were washed three times with saturated aqueous sodium bicarbonate solution and the combined washings were back extracted once with ether. The total organic solution was dried, filtered and concentrated at reduced pressure giving 5.93 g. (92.5%) of 4-(3-oxo-6-cyano-1-hexyl)-3-a,4,7,7a-tetrahydro-7a-methyl-1,5(6H)-indandione as an orange oil.

ir: $\nu_{max}^{film}$ 2250 (C ≡ N), 1745 (cyclopentanone C=O), 1715 (cyclohexanone and aliphatic C=O) cm$^{-1}$. TLC analysis showed the major spot due to the triketone with $R_f$ 0.28.

EXAMPLE 9

A solution of 3.983 g. (0.01066 mole) of crude triketone prepared in Example 8 in 20 ml. of methanol was treated with 10 ml. of 0.1M methanolic potassium hydroxide solution. The resulting dark brown solution was stirred and refluxed for 2 hours. After cooling, the reaction mixture was poured into brine and extracted twice with ether and once with methylene chloride. The combined organic extracts were dried, filtered and concentrated at reduced pressure giving 2.8 g. (93.8%) of crude trans-anti-6-(2-cyanoethyl)-3a-methyl-1,2,3a,4,5,9,9a,9b-octahydro-3H-benz[e]inden-3,7(8H)-dione as a brown solid. Recrystallization from ethanol gave 1.5 g. (50.2%) of pale yellow crystals, m.p. 105°–107° (homogeneous on tlc analysis, $R_f$ 0.33). The analytical specimen was obtained as white crystals, m.p. 106°–107°, by further recrystallization of a sample from ethanol.

ir: $\nu_{max}^{CHCl_3}$ 2250 (C ≡ N), 1740 (cyclopentanone C=O), 1665 (cyclohexenone C=O), 1605 (C=C) cm$^{-1}$;

uv: $\lambda_{max}^{EtOH}$ 245 (ε15640) mμ, nmr: $\delta_{TMS}^{CDCl_3}$ 1.03 (singlet, C$_{13}$—CH$_3$) ppm.

Anal. calcd. for $C_{17}H_{21}NO_2$: C, 75.24; H, 7.80; N, 5.16; Found: C, 75.51; H, 7.99; N, 5.08.

EXAMPLE 10

A solution of 2.853 g. (0.0099 mole) of crude triketone prepared in Example 8 and 0.637 g. of p-toluenesulfonic acid monohydrate in 130 ml. of toluene was stirred and refluxed, under nitrogen using a Dean-Stark trap for 4.5 hours after vigorous refluxing began. The mixture was allowed to stir at room temperature for 13.5 hours then washed twice with saturated aqueous sodium bicarbonate solution. The combined washings were back extracted twice with methylene chloride. The combined organic solutions were dried, filtered and concentrated at reduced pressure giving 2.728 g. of an orange semi-solid residue.

This material was triturated under ethyl acetate and the solid was suction filtered and washed until essentially colorless with ethyl acetate. The combined filtrate and washings were concentrated at reduced pressure and the residue chromatographed on 100 g. of silica gel. The fractions eluted with 4:1 benzene: ethere gave 0.866 g. (32.3%) of crystalline 6-(2-cyanoethyl)-3a-methyl-1,2,3a,4,5,9,9a,9b-octahydro-3H-benz[e]inden-3,7(8H)-dione. This was recrystallized from ethanol giving 0.681 g. of pale-yellow solid, m.p. 105°–107°.

EXAMPLE 11

A solution of 1.03 g. (3.82 moles) of enedione prepared in Example 9 in 25 m. of dry tetrahydrofuran and 0.7 ml. of triethylamine was stirred in an atmosphere of hydrogen over 0.25 g. of preequilibrated AK-4 5% palladium on carbon. After 40 minutes, 102 ml. of hydrogen was absorbed (96 ml. theory) and the hydrogenation was stopped. The catalyst was filtered and washed with ether and the combined filtrate and washings were concentrated at reduced pressure giving 1 g. of colorless, solid residue. This was crystallized from ethanol giving 805 mg. (77.4%) of colorless trans-anti-trans-anti-6-(2-cyanoethyl)-3a-methyl-1,2,3a,4,5-,5a,8,9,9a,9b-decahydrobenz[e]inden-3,7(6H)dione, m.p. 130°–132°. TLC analysis showed a single spot, $R_f$ 0.31 (no uv.). An analytical specimen was obtained, m.p. 132°–133°, by further recrystallization from ethanol.

ir: $\nu_{max}^{CHCl_3}$ 2250 (C ≡ N), 1740 (cyclopentanone C=O), 1710 (cyclohexanone C=O) cm$^{-1}$;

nmr: $\delta_{TMS}^{CDCl_3}$ 0.98 (singlet, C$_{3a}$–C$\underline{H}_3$) ppm; mass spectrum m/e 273 (M$^+$).

Anal. calcd. for $C_{17}H_{23}NO_2$: C, 74.69; H, 8.48; N, 5.12; Found: C, 74.49; H, 8.49; N, 5.05.

EXAMPLE 12

A solution of 0.1 g. (0.366 mole) of cyanodione prepared in Example 11, 0.22 ml. of trimethylorthoformate, 0.02 ml. of borontrifluoride etherate and 10 ml. of methanol was stirred at room temperature for 0.5 hours then poured into excess saturated, aqueous sodium bicarbonate solution and extracted three times with ether. The combined ether extracts were washed with brine, dried, filtered and concentrated at reduced pressure giving 0.121 g. of an oil. TLC analysis showed an elongated spot, $R_f$ 0.48 and no starting material present.

ir: $\nu_{max}^{film}$ 2250 (C ≡ N), 2840 (OCH$_3$), 1680 (enolether), 1160, 1110, 1080, 1050 cm$^{-1}$ (no OH, essentially no C=O). The nmr spectrum showed OCH$_3$ singlets at $\delta_{TMS}^{CDCl_3}$ 3.28, 3.24 and 3.22 ppm and a weak band at δ3.50 possibly due to the vinyl proton of an enolether. The integration indicated 3 OCH$_3$ groups per molecule.

The mixture appeared to consist of trans-anti-trans-anti-3,3,7,7-tetramethoxy-3a-methyl-6(2-cyanoethyl-perhydro-1H-benz-[e]indene and an enol ether at the 6,7- or 7,8-position resulting from loss of one molecule of methanol.

EXAMPLE 13

A solution of 0.134 g. of the crude ketal-enolether mixture from Example 12 in 10 ml. of anhydrous ether was stirred with cooling in an ice-salt bath at −10°–0° while 0.8 ml. (1.6 moles) of 2M ethereal methyllithium was quickly added from a syringe. The resulting mixture was stirred at −10°–0° for 1.5 hours then treated with saturated aqueous ammonium chloride solution. The ether layer was separated and the aqueous layer was extracted twice with ether. The combined ether solutions were washed with saturated brine, dried, filtered and concentrated at reduced pressure. This gave 0.147 g. of pale-yellow oily mixture of trans-anti-trans-anti-3,3,7,7-tetramethoxy-3a-methyl-6(3-oxo-1-butyl)-perhydro-1H-benz[e]indene and the corresponding enol ether. The infrared spectrum indicated the reaction was complete:

$\nu_{max}^{film}$ 2835 (OCH$_3$), 1710 (ketone C=O), 1680 (enolether) cm$^{-1}$ (no C ≡ N).

EXAMPLE 14

A solution of 0.1 g. (0.366 mole) of trans-anti-trans-anti-6-(2-cyanoethyl)-3a-methyl-1,2,3a,4,5,5a,8,9-,9a,9b-decahydrobenz [e]inden-3,7(6H)dione in 5 ml. of dry tetrahydrofuran was treated with 0.226 g. (3.66 moles) of ethylene glycol, 0.2 ml. of trimethyl orthoformate and 0.01 ml. of concentrated sulfuric acid. The resulting solution was stirred at room temperature under nitrogen, for 1.5 hours then poured into excess 10% aqueous sodium hydroxide solution. After dilution with brine, the mixture was extracted three times with ether. The combined ether extracts were washed with brine, dried, filtered and concentrated at reduced pressure giving 133 mg. of colorless, crystalline product. TLC analysis showed a major spot, $R_f$ 0.50 and a very weak impurity $R_f$ 0.76. No starting material, $R_f$ 0.40 was detectable.

This material was combined with the product from an identical run (0.111 g.; 0.244 g. total) and chromatographed on 25 g. of silica gel. The fractions eluted with 1:1 benzene:ether gave 0.229 g. (86.8%) of pure trans-anti-trans-anti-3,3,7,7-bis(ethylenedioxy)-3a-methyl-6-(2-cyanoethyl)perhydro-1H-benz[e]idene as a colorless solid. (TLC, $R_f$ 0.5). Two recrystallizations from ether gave colorless crystals, m.p. 118.5°–120.5°.

ir: $\nu_{max}^{CHCl_3}$ 2250 (C ≡ N), 1160, 1105, 1050 cm$^{-1}$;

nmr: $\delta_{TMS}^{CDCl_3}$ 3.94, 3.86 (singlets, 8 ethylene ketal protons), 0.87 (singlet, C$_{3a}$–C$\underline{H}_3$) ppm; mass spectrum m/e 361 (M$^+$).

Anal. calcd. for $C_{21}H_{31}NO_4$: C, 69.77; H, 8.65; N, 3.88; Found: C, 69.87; H, 8.39; N, 3.86.

EXAMPLE 15

An ethereal methyllithium solution (4.3 ml.; 2M; 8.6 moles) was cooled to −10° (ice-salt bath) and stirred while a solution of 0.711 g. (1.97 moles) of bis-ketal nitrile prepared in Example 14 in 15 ml. of anhydrous ether and 5 ml. of anhydrous tetrahydrofuran was added over a 3 minute period. The reaction mixture was stirred at −5° for 1 hour then 10 ml. of water was added and stirring was continued at room temperature for 30 minutes. After dilution with saturated brine, the ether layer was separated and the aqueous layer was extracted with ether. The combined ether layers were washed with brine, dried, filtered and concentrated at reduced pressure giving 0.719 g. (96.5%) of essentially pure trans-anti-trans-anti-3,3,7,7-bis(ethylenedioxy)-3a-methyl-6-(3-oxo-1-butyl)perhydro-1H-benz[e]indene as a colorless solid. TLC analysis showed essentially one spot $R_f$ 0.37.

A sample was chromatographed on silica gel and recrystallized from ether giving fluffy white solid, m.p. 122°–123°.

ir: $\nu_{max}^{CHCl_3}$ 1715 (aliphatic ketone C=O), 1160, 1105, 1050, 1040, 950 cm$^{-1}$.

EXAMPLE 16

A solution of 0.088 g. (0.23 mole) of the crude mixture from Example 13 in 5 ml. of methanol and 1 ml. of 4N aqueous hydrochloric acid solution was stirred and refluxed for 4 hours. After cooling, the reaction mixture was diluted with benzene and washed with saturated brine. The organic layer was dried, filtered and concentrated at reduced pressure giving 0.063 g. of crude, crystalline 19-norandros-4-en-3,17-dione. TLC analysis showed the main spot $R_f$ 0.27 (identical $R_f$ to that of authentic 19-norandrostendione) and a minor impurity, $R_f$ 0.42.

This material was chromatographed on 5 g. of silica gel. The fractions eluted with 4:1 and 1:1 benzene:ether afforded 0.053 g. (84.8%) of colorless crystals which were homogeneous on TLC analysis. Recrystallization from aqueous methanol gave 0.038 g. (60.8%) of colorless crystals, m.p. 155°–157°.

ir: $\nu_{max}^{CHCl_3}$ 1735 (cyclopentanone C=O), 1665 (enone C=O), 1620 (C=C)$^{-1}$;

uv: $\nu_{max}^{EtOH}$ 240 $\mu$ ($\epsilon$15650).

EXAMPLE 17

A solution of 0.538 g. (1.47 moles) of bis-ketal from Example 15 in 20 ml. of methanol and 6 ml. of 4N aqueous hydrochloric acid was stirred and refluxed for 4 hours, then cooled, diluted with brine and extracted three times with ether. The combined ether extracts were washed with brine, dried, filtered and concentrated at reduced pressure giving 0.352 g. (87%) of colorless, crystalline 19-norandrostendione. This material was homogeneous on TLC analysis, $R_f$ 0.36. Recrystallization from aqueous methanol gave 0.254 g. (62.7%) of colorless crystals, m.p. 155°–156.5°.

uv: $\lambda_{max}^{EtOH}$ 240 m$\mu$ ($\epsilon$17400).

EXAMPLE 18

An 18.0 g. sample of 2-ethylcyclopentan-1,3-dione was dissolved in 500 ml. of 4:1 toluene:glacial acetic acid and treated with a solution of 20.15 g. of Mannich base from Example 4 in 200 ml. of 4:1 toluene:glacial acetic acid. The resulting solution was stirred and heated under reflux for 0.5 hour then refluxed azeotropically for 1.5 hour using a Dean-Stark trap. After cooling to room temperature, the mixture was diluted with 100 ml. of toluene and washed with water (2 × 200 ml.). Each aqueous portion was reextracted with toluene (2 × 200 ml.). The combined organic extracts were washed with saturated brine (1 × 200 ml.) then dried, filtered and concentrated at reduced pressure giving 20.38 g. (93.5%) of 3-(3-cyanopropyl)-6a-ethyl-1,2,3,5,6,6a-hexahydrocyclopenta[f][1]benzopyran-7(8H)-one which showed one spot, $R_f$ 0.50, on TLC analysis.

From another experiment, on a smaller scale, using the same procedure as above, the crude product was purified by chromatography on silica gel. Elution with 9:1 and 4:1 benzene:ether gave pure dienolether mixture.

ir: $\nu_{max}^{CHCl_3}$ 2250 (C ≡ N), 1730 (cyclopentanone) (C=O), 1640 (dienolether) cm$^{-1}$;

uv: $\lambda_{max}^{EtOH}$ 254 m$\mu$ ($\epsilon$12650);

nmr: $\delta_{TMS}^{CDCl_3}$ 5.51 (triplet, J=2Hz, —C$\underline{H}$=C, 1 proton), and 3.80 (multiplet, C$_3$—H, 1 proton), 2.94 (multiplet, C$_8$—H, 2 protons) and 0.83 (triplet, J=8Hz, 6a—CH$_2$CH$_3$, 3 protons) ppm.

Anal. Calcd. for C$_{18}$H$_{23}$NO$_2$: C, 75.75; H, 8.12; N, 4.91; Found: C, 75.50; H, 7.88; N, 4.76.

EXAMPLE 19

The crude mixture of dienolether from Example 18 (20.38 g.) in 120 ml. of benzene was added to a stirred solution of 6 g. of sodium borohydride in 150 ml. of ethanol and 15 ml. of water at 0°. The reaction mixture was stirred at 0° for 30 minutes then at room temperature for 1 hour. Water (200 ml.) was added along with 100 ml. of benzene. The organic phase was separated and the aqueous phase was extracted three times with benzene. Each organic extract was washed twice with saturated brine, then combined, dried, filtered and concentrated at reduced pressure giving 21.7 g. of yellow-orange 3-(3-cyanopropyl)-6a-ethyl-1,2,3,5,6,6a,7,8-octahydrocyclopenta[f][1]benzopyran-7β-ol. TLC analysis showed a single spot, $R_f$ 0.48 and no starting ketone.

ir: $\nu_{max}^{film}$ 3450 (OH), 2250 (C ≡ N) and 1650 (dienolether) cm$^{-1}$.

EXAMPLE 20

The dienolether from Example 19 (21.7 g.) in 500 ml. of toluene was hydrogenated over 4 g. of AK-4 5% palladium on carbon at room temperature and 1 atmosphere for 6 hours. A total of 1725 ml. of hydrogen was absorbed during this period. The catalyst was filtered with suction through celite and the filter cake was washed well wth fresh toluene. The combined filtrate and washings were concentrated at reduced pressure giving 20.15 g. of yellow oily 6a,9a-trans-3-(3-cyanopropyl)-6a-ethyl-1,2,3,5,6,6a,7,8,9,9a-decahydrocyclopenta[f][1]benzopyran-7β-ol.

ir: $\nu_{mas}^{film}$ 3475 (OH), 2250 (C ≡ N), 1680 (enolether) cm$^{-1}$; the band at 1650 cm$^{-1}$ due to the dienolether was absent.

EXAMPLE 21

The above crude enolether from Example 20 (20.15 g.) was dissolved in 200 ml. of acetone containing 25 ml. of 1N aqueous sulphuric acid. The solution was stirred at room temperature for 1 hour after which time TLC analysis showed the absence of starting material.

The reaction mixture which contained 6a,9a-trans-3-(3-cyanopropyl)-6a-ethyl-perhydrocyclopenta[f][1]benzopyran-4a,7β-diol was cooled to 0° – 5° (icebath) while 80 ml. of Jones reagent was added dropwise over 20 minutes. After stirring at room temperature for 3 hours, the excess oxidizing agent was decomposed with sodium bisulfite solution. Saturated brine (200 ml.) was added and the mixture was extracted with benzene (3 × 200 ml.). Each benzene extract was washed with saturated aqueous sodium bicarbonate solution (2 × 200 ml.) and brine (2 × 200 ml.). The combined organic solution as dried, filtered and concentrated at reduced pressure giving 14.2 g. (66%) of red, 3a,7a-trans-4-(3-oxo-6-cyano-1hexyl)-3a,4,7,7a-tetrahydro-7a-ethyl-1,5(6H)-indandione.

ir: $\nu_{max}^{film}$ 2250 (C ≡ N), 1740 (cyclopentanone C=O), 1715 (saturated aliphatic and cyclohexanone C=O) cm$^{-1}$ (no OH present).

EXAMPLE 22

A 6.0 g. sample of the crude triketone from Example 21 was dissolved in 5o ml. of ethanol and 25 ml. of 0.1N methanolic potassium hydroxide then stirred and heated under reflux for 1.5 hours. The methanol was evaporated at reduced pressure and the residue was treated with saturated brine (100 ml.) and extracted with benzene (3 × 200 ml.). Each benzene extract was washed with brine (2 × 100 ml.). The combined organic extracts were dried, filtered and concentrated at reduced pressure giving 5.3 g. of dark red, oily product.

uv: $\lambda_{max}^{EtOH}$ 246 mμ(ε10300), 300 (915).

This material was chromatographed on 250 g. silica gel. The fractions eluted with 4:1 and 2:1 benzene:ether which were homogeneous on TLC analysis ($R_f$ 0.4; strong uv spot) gave 2.55 g. of pale-yellow oil. The other fractions (1.10 g.) showed the presence of a slower moving impurity, $R_f$ 0.3 (~70% desired material present).

One of the purer fractions was rechromatographed on silica gel giving trans-anti-6-(2-cyanoethyl)-3a-ethyl-1,2,3a,4,5,9,9a,9b-octahydro-3H-benz[e]inden-3,7(8H)-dione as a colorless oil with the following physical properties:

ir: $\nu_{max}^{CHCl_3}$ 2255 (C ≡ N), 1740 (cyclopentanone C=O), 1670 (α, β-unsaturated ketone C=O), 1600 (C=C) cm$^{-1}$;

nmr: $\delta_{TMS}^{CDCl_3}$ 0.86 (triplet, J=8Hz, 3a-CH$_2$CH$_3$, 3 protons) ppm.

uv: $\lambda_{max}^{EtOH}$ 245/6 mμ(ε=12,600).

Anal. calcd. for C$_{18}$H$_{23}$NO$_2$: C, 75.75; H, 8.12; N, 4.91; Found: C, 75.79; H, 7.99; N, 4.91.

EXAMPLE 23

A 4.0 g. sample of the crude triketone from Example 21 was dissolved in 200 ml. of toluene and 0.90 g. of p-toluenesulfonic acid monohydrate was added. The mixture was stirred and brought to reflux over 1 hour then refluxed with azeotropic removal of water (Dean-Stark trap) for 4 hours. After cooling to room temperature, the reaction mixture was washed with saturated aqueous sodium bicarbonate (2 × 100 ml.), and saturated brine (1 × 100 ml.). The aqueous washings were back extracted with methylene chloride (3 × 100 ml.). The combined organic extracts were dried, filtered and concentrated at reduced pressure giving 3.5 g. of an orange semi-solid residue.

This material was triturated under ethyl acetate and the solid was filtered off and washed well with ethyl acetate until nearly colorless. The combined filtrate and washings from the above purification were concentrated at reduced pressure and the residue was chromatographed on 140 g. of silica gel. The fractions eluted with 4:1 and 2:1 benzene:ether gave 0.95 g. (25.2%) of pale-yellow oil. The ir spectrum and TLC of this material were identical to that of enedione prepared in Example 22.

EXAMPLE 24

A 1.15 g. sample of enedione from Example 22 (purified by chromatography) was dissolved in 40 ml. of dry tetrahydrofuran containing 1 ml. of triethylamine and hydrogenated over 0.2 g. of AK-4 (5% palladium on carbon) at room temperature and one atmosphere for 2.5 hours. The hydrogen uptake amounted to 121 ml. The catalyst was filtered with suction through celite and the filtrate was concentrated at reduced pressure giving 1.14 g. of colorless oily trans-anti-trans-anti-6-(2-cyanoethyl)-3a-ethyl-1,2,3a,4,5,5a,8.9.9a,9b-decahydrobenz[e]inden-3,7(6H) dione. TLC analysis showed a single spot $R_f$ 0.4.

This material was chromatographed on 50 g. of silica gel. The fractions eluted with 9:1, 4:1 and 2:1 benzene:ether afforded 0.906 g. (78.5%) of colorless crystals. Recrystallization from 2-propanol gave the analytical specimen as colorless crystals, m.p. 118.5°–121.0°.

ir: $\nu_{max}^{CHCl_3}$ 2250 (C ≡ N), 1740 (cyclopentanone C=O), 1715 (cyclohexanone C=O) cm$^{-1}$.

Anal. calcd. for C$_{18}$H$_{25}$NO$_2$: C, 75.22; H, 8.77; N, 4.87; Found: C, 75.40; H, 9.07; N, 4.87.

EXAMPLE 25

A pure sample of dione from Example 24 (0.2 g.) was dissolved in 5 ml. of dry tetrahydrofuran and treated with 0.5 ml. of ethylene glycol, 0.5 ml. of trimethylorthoformate and 0.01 ml. of concentrated sulfuric acid. The resulting solution was stirred at room temperature for 5.5 hours. At the end of this time TLC analysis showed a single spot, $R_f$ 0.48 and no starting material present. After addition of several drops of triethylamine then 2 ml. of 10% aqueous sodium hydroxide, the mixture was extracted three times with benzene. The combined organic extracts were washed twice with saturated brine, dried, filtered and concentrated at reduced pressure giving 0.264 g. (100%) of crude trans-anti-trans-anti-3,3,7,7-bis(ethylenedioxy)-3a-ethyl-6(2-cyanoethyl)perhydro-1H-benz[c]indene as a beige powder. Recrystallization from 2 propanol gave 0.214 g. of colorless crystals, m.p. 127.5°–129.5°.

ir: $\nu_{max}^{CHCl_3}$ 2250 (C ≡ N), 1160, 1100, 1050 cm$^{-1}$;

nmr: $\delta_{TMS}^{CDCl_3}$ 3.96, 3.86 (singlets, 8 ethylene ketal protons) ppm.

Anal. calcd. for C$_{22}$H$_{33}$NO$_4$: C, 70.37; H, 8.86; N, 3.73; Found: C, 70.32; H, 8.56; N, 3.52.

EXAMPLE 26

A solution of 0.164 g. of pure diketal nitrile from Example 25 in 25 ml. of anhydrous ether was added dropwise from a syringe to a solution of 2 ml. of ~2M ethereal methyllithium in 5 ml. of anhydrous ether at −15°. The mixture was stirred at −10° for 1.75 hours then decomposed by the addition of 2 ml. of water at 0°. After stirring at room temperature for 1.5 hours, the mixture was extracted three times with ether and the combined ether extracts were washed twice with saturated brine, dried, filtered and concentrated at reduced pressure. This gave 0.165 g. (97%) of trans-anti-trans-anti-3,3,7,7-bis(ethylenedioxy)-3a-ethyl-6-(3-oxo-1-butyl)perhydro-1H-benz[e]indene as a beige solid. TLC analysis showed a major spot, $R_f$ 0.42 and a trace of a faster moving spot, the $R_f$ of which corresponded to that of the starting nitrile.

This material was recrystallized from 2-propanol giving 0.082 g. of colorless, fluffy crystals, m.p. 116°–119°.

ir: $\nu_{max}^{CHCl_3}$ 1710 (ketone C=O), 1155, 1100, 1055 cm$^{-1}$;

nmr: $\delta_{TMS}^{CDCl_3}$ 3.88, 3.82 (singlets, 8 ethylene ketal protons), 2.06 singlet, C$\underline{H}_3$—C—O, 3 protons) ppm.

EXAMPLE 27

A solution of 0.124 g of diketal from Example 26 in 7 ml. of methanol and 2 ml. of 4N aqueous hydrochloric acid was refluxed for 4 hours. After cooling to room temperature, the reaction mixture was treated with saturated brine and extracted three times with benzene. The combined organic extracts were washed once with saturated aqueous sodium bicarbonate solution, once with brine, dried, filtered and concentrated at reduced pressure. This gave 0.110 g. of crude, yellow crystalline 13β-ethylgon-4-en-3,17-dione which showed essentially one strongly UV fluorescent spot, R$_f$ 0.4 on TLC analysis.

This material was chromatographed on 5 g. of silica gel. The fractions eluted with 2:1 and 1:1 benzene:ether gave 0.083 g. (92%) of pale-yellow crystalline material. Recrystallization from methanol afforded 0.056 g. of pure product as colorless crystals, m.p. 156°–159°.

ir: $\nu_{max}^{CHCl_3}$ 1735 (cyclopentanone C=O), 1670 (α,β-unsaturated ketone C=O), 1625 (C=C) cm$^{-1}$;

uv: $\lambda_{max}^{EtOH}$ 230 mμ(ε18000);

nmr: $\delta_{TMS}^{CDCl_3}$ 5.82 (singlet, C$_4$—$\underline{H}$, 1 proton), 0.81 (triplet, —CH$_2$C$\underline{H}_3$, 3 protons) ppm.

EXAMPLE 28

A 16.7 g. (0.1 mole) sample of the lactone prepared in Example 3 was treated with 76 ml. (0.16 mole) of 2.1M vinyl-magnesium chloride solution in THF using the procedure described in Example 4. After the same work-up, the THF extracts [containing 6-(3-cyanopropyl)-2-vinyltetrahydropyran-2-ol] were then treated with 12.1 g. of (−)-S-α-methylbenzylamine and left at room temperature for 3 hours. The solvents were removed at reduced pressure and the residue was dissolved in a mixture of 125 ml. of acetone and 125 ml. of 1.5N aqueous sulfuric acid solution. After 15 minutes at room temperature this mixture was extracted with 100 ml. of n-hexane and the hexane extract was reextracted with 30 ml. of 1:1 acetone:1N aqueous sulphuric acid.

The combined acid aqueous extract was made alkaline with 10% aqueous sodium carbonate solution and the Mannich base (2-[2-(S-α-phenethylamino9ethyl]-6-(3-cyanopropyl)-tetrahydropyran-2-ol) was isolated by ether extraction of (1 × 100 ml.; 3 × 50 ml.). The combined ether solutions were washed with brine, dried and concentrated at reduced pressure giving 28.5 g. of residue.

This material was dissolved in 65 ml. of acetone and added to a solution of 9.2 g. of oxalic acid in 65 ml. of acetone and left at room temperature for 24 hours. The solids were filtered with suction and washed with 25 ml. of acetone and 60 ml. of 1:1 acetone:isopropyl ether mixture and dried under high vacuum over P$_2$O$_5$. The white solid (10.5 g., m.p. 107°–111° (Hot Stage), [α]$_D$-33.8°) was recrystallized from 50 ml. of acetonitrile to yield 9.33 g. (46%) of pure 2S, 6R 2-[2-(S-a-phenethylamino)ethyl]-6-(3-cyanopropyl)-tetrahydropyran-2-ol oxalate m.p. 108°–12° (Hot Stage), [α]$_D$-36.6° (C=2.26,CH$_3$OH). The analytical specimen, obtained by several recrystallizations of a sample from acetone showed m.p. 108°–109° (capillary), [α]$_D$-35.28° (C=1.0, CH$_3$OH).

Anal. calcd. for C$_{19}$H$_{28}$N$_2$O$_2$. C$_2$H$_2$O$_4$: C, 62.05; H, 7.44; N, 6.89; Found: C, 62.37; H, 7.65; N, 6.84.

EXAMPLE 29

To a suspension of 6.1 g. of oxalate from Example 28 in 60 ml. of water, sodium carbonate was added until the mixture showed pH 9. The free base was then extracted with several portions of ether.

The combined ether extracts were washed with brine, dried, filtered, concentrated at reduced pressure and dried under high vacuum giving 4.65 g. of 2S,6R,2-[2-(S-α-phenethylamine)ethyl]-6-(3-cyanopropyl)tetrahydropyran-2-ol as a light yellow oil. [α]$_D^{25}$-20.39° (C=0.9759 in benzene). ir: $\nu_{max}^{CHCl_3}$ 3100 (bonded OH, NH), 2250 (C ≡ N) cm$^{-1}$.

Anal. calcd. for C$_{19}$H$_{28}$N$_2$O$_2$: C, 72.11; H, 8.92; N, 8.85; Found: C, 72.17; H, 8.85; N, 9.05.

EXAMPLE 30

A mixture of 4.55 g. of the free base from Example 29 110 ml. of methanol, 0.460 g. of sodium bicarbonate and 2.0 g. of freshly distilled benzaldehyde was stirred and heated at reflux for 8.5 hours. The reaction mixture was then concentrated to a volume of 10 ml., diluted with saturated brine and extracted with methylene chloride. The combined organic extracts were washed with brine, dried, filtered and concentrated at reduced pressure giving 6.4 g. of oily product. This was chromatographed on 65 g. of silica gel. Elution with ether, 4:1 and 2:1 ether:ethyl acetate afforded 3.07 g. (92%) of pure 2S,6R, 2-(2-methoxyethyl)-6-(3-cyanopropyl) tetrahydropyran-2-ol as an oil.

ir: $\nu_{max}^{film}$ 3470 (OH), 2250 (C ≡ N), and 1720 (ketone C=O) cm$^{-1}$.

EXAMPLE 31

A mixture of 2.27 g. of methanol adduct from Example 30 1.35 g. of 2-methylcyclopentan-1,3-dione, 40 ml. of toluene and 20 ml. of acetic acid was stirred and heated at 110° for 5 hours. The bath temperature was then raised to 140° for 1 hour, during which time azeotropic distillation of water into a Dean-Stark trap was carried out. The cooled mixture was washed with saturated brine, saturated aqueous sodium bicarbonate solution and again with brine. The aqueous washings were reextracted with benzene and the combined benzene solutions were dried. Filtration and solvent removal afforded 2.8 g. of a crude, crystalline mixture of 3S,6aS and 3S,6a R-3(3-cyanopropyl)-6a-methyl-1,2,3,5,6,6a-hexahydrocyclopenta[f][1]benzopyran-7(8H)-one which was chromatographed on 250 g. of silica gel. The fractions eluted with 19:1 benzene:ether furnished 2.02 g. of solid m.p. 72°–96°, [α] $_D^{25}$—150.86° (C=0.9207 in chloroform).

This material was recrystallized from 9 ml. of 2-propanol giving 1.02 g. (37.7%) of pure 3S,6aS,3-(3-cyanopropyl)-6a-methyl-1,2,3,5,6,6a-hexahydrocyclopenta[f][1]benzopyran-7(8H)-one m.p. 101°–104°, [α]$_D^{25}$—182.0° (C=1.0 in chloroform). A sample was recrystallized several times to afford an analytical sample m.p. 102°–104°, [α]$_D^{25}$—184.42° (C=1.0335 in CHCl$_3$).

ir: $\nu_{max}^{CHCl_3}$ 2250 C ≡ N), 1740 (cyclopentanone C=O) and 1640 (dienolether) cm$^{-1}$; uv: $\lambda_{max}^{EtOH}$ 254 mμ(ε18800); nmr: $\delta_{TMS}^{CDCl_3}$ 5.41 (triplet, J=2Hz, H—C=, 1 proton); 3.78 (multiplet, H—C—O, 1 proton), 1.10 (singlet, $C_{3a}$—$CH_3$, 3 protons) ppm.

Anal. calcd. for $C_{17}H_{21}NO_2$: C, 75.24; H, 7.80; Found: C, 75.17; H, 7.95.

EXAMPLE 32

A solution of 1.02 g. of dienolether from Example 31 in 6 ml. of ethanol and 5 ml. of benzene was added dropwise to a stirred solution of 0.25 g. of sodium borohydride in 5 ml. of water and 5 ml. of ethanol at 0°. After stirring at room temperature for 15 minutes, the reaction mixture was poured into water and extracted with methylene chloride. The combined organic extracts were washed with brine, dried, filtered and concentrated at reduced pressure affording 1.01 g. of 3S,6aS,3-(3-cyanopropyl)-6a-methyl-1,2,3,5,6,6a,7,8-octahydrocyclopenta[f][1]benzopyran7β-ol, m.p. 115°–120°, $[\alpha]_D^{25}$ —190.68° (C=0.9348 in chloroform). A sample was recrystallized from 2-propanol at −15° to give an analytical sample, m.p. 116°–119°, $[\alpha]_D^{25}$ —194.57° (C=1.012 in CHCl$_3$).

ir: $\nu_{max}^{CHCl_3}$ 3650 (OH), 2250 (C ≡ N) and 1640 (dienolether) cm$^{-1}$;

uv: $\lambda_{max}^{EtOH}$ 254 mμ($\epsilon$19300); nmr: $\delta_{TMS}^{CDCl_3}$ 5.01 (multiplet, H—C=, 1 proton), 3.93 (multiplet, H—C—OH), 3.73 (multiplet, H—C—O), 0.93 (singlet, $C_{6a}$—$CH_3$, 3 protons) ppm.

Anal. calcd. for $C_{17}H_{23}NO_2$: C, 74.69; H, 8.48; Found: C, 74.55; H, 8.61.

EXAMPLE 33

A solution of 0.75 g. of dienolether from Example 32 in 15 ml. of dry ether and 5 ml. of dry tetrahydrofuran was added dropwise to 11 ml. of a 2M ethereal methylmagnesium chloride solution with stirring, at 0°. The reaction mixture was stirred at 0° for 1 hour and at room temperature for 4 hours, then poured into saturated aqueous ammonium chloride solution and extracted with ether. The combined ether extracts were washed with brine and dried. Filtration and solvent removal gave 0.569 g. of crude product which was chromatographed on 30 g. of silica gel. The fractions eluted with 2:1 and 1:1 benzene:ether and ether alone afforded pure, crystalline 3S,6aS-3-(4-oxo-1-pentyl)-6a-methyl-1,2,3,5,6,6a,7,8-octahydrocyclopenta[f][1]benzopyran-7β-ol (0.151 g.), $[\alpha]_D^{25}$—165.17° (C=0.689 in CHCl$_3$).

ir: $\nu_{max}^{CHCl_3}$ 3620 (OH) 1720 (ketone C=O) and 1640 (dienolether) cm$^{-1}$; uv: $\lambda_{max}^{EtOH}$ 254 mμ($\epsilon$18320).

EXAMPLE 34

A mixture of 130.5 mg. of dienolether from Example 33, 15 ml. of xylene and 1.3 g. of silver carbonate-celite reagent was stirred and heated under reflux for 1 hour. After cooling, the solids were filtered off and washed several times with benzene. The filtrate was evaporated at reduced pressure to give 100 mg. of crude product which was chromatographed on 20 g. of silica gel. Elution with 19:1 and 4:1 benzene:ether gave 60 mg. of 3S,6aS,3-(4-oxo-1-pentyl)-6a-methyl-1,2,3,5,6,6a-hexahydrocyclopenta[f][1]benzopyran-7(8H)-one m.p. 67°–70°, $[\alpha]_D^{25}$—157.95° (C=0.9883 in CHCl$_3$). This material was recrystallized from aqueous methanol to give a pure sample m.p. 72.5°–74°, $[\alpha]_D^{25}$—163.90 (C=1.0427 in CHCl$_3$);

ir: $\nu_{max}^{CHCl_3}$ 1740 (cyclopentanone C=O), 1710 (ketone C=O) and 1640 (dienolether) cm$^{-1}$; uv: $\lambda_{max}^{EtOH}$ 253 mμ($\epsilon$19000).

EXAMPLE 35

A solution of methanol adduct from Example 30 (605 mg.) in methanol (6.0 ml.) and trimethylorthoformate (0.9 ml.) was treated with borontrifluoride etherate (60 mg.). After the resulting mixture was stirred at room temperature for 15 minutes, it was treated with an additional 30 mg. of borontrifluoride etherate and stirred for another 15 minutes at room temperature. The mixture was then poured into excess sodium bicarbonate solution and the resulting mixture was extracted with ether three times. The combined ether extract was washed with brine and then dried. Filtration and solvent removal afforded crude 2S, 6R-2-methoxy-2-(2-methoxyethyl)-6-(3-cyanopropyl)-tetrahydropyran (590 mg.) as an oil. ir: $\nu_{max}^{film}$ 2250 (C ≡ N) cm$^{-1}$. The absence of hydroxyl and ketone in the ir indicated that the reaction was complete. Chromatography on silica gel and elution with benzene:ether 9:1 and 4:1 afforded a pure sample $[\alpha]_D^{25}$—72.97° (C=1.1238 in chloroform) or $[\alpha]_D^{25}$—63.46° (C=1.0385 in benzene);

ir: $\nu_{max}^{CHCl_3}$ 2250 (C ≡ N) cm$^{-1}$; nmr: $\delta_{TMS}^{CDCl_3}$ 3.30, 3.15 (singlets, 6 methoxy protons) ppm.

Anal. calcd. for $C_{13}H_{23}NO_3$: C, 64.69; H, 9.61; N, 5.80; Found: C, 64.82; H, 9.76; N, 5.58.

EXAMPLE 36

An ethereal methyllithium solution (11 ml.; 2M) was cooled to −15° and stirred while a solution of the product from Example 35 (1.25 g.) in ether (35 ml.) was added over a 10 minute period. After the resulting mixture was stirred for 30 minutes at −10° an aliquot was removed and tracted with excess saturated aqueous bicarbonate solution. Th TLC analysis showed essentially one spot ($R_f$ 0.35) plus some minor polar spots ($R_f$ 0.15 and 0.05). The absence of starting material ($R_f$ 0.4) indicated that the reaction was complete. The reaction mixture was then allowed to warm up to −5° C. and was treated with excess saturated bicarbonate solution. The resulting mixture was stirred at room temperature for 1 hour. The aqueous layer was then separated and extracted three times with ether. The combined ether layers were washed with brine and dried. Filtration and solvent removal afforded crude 2S, 6S-2-methoxy-2-(2-methoxyethyl)6-(4-oxo-1-pentyl)-tetrahydropyran (1.24 g.) as an oil. Chromatography on silica gel and elution with benzene-ether 1:1 afforded a pure sample as a colorless oil. $[\alpha]_D^{25}$—66.55° (C=1.0684 in chloroform) or $[\alpha]_D^{25}$—63.47° (C=1.010 in benzene);

ir: $\nu_{max}^{CHCl_3}$ 1710 (ketone C=O) cm$^{-1}$; nmr: $\delta_{TMS}^{CDCl_3}$ 3.31, 3.16 (singlets 6 methoxy protons) 2.13 (singlet, $CH_3CO$; 3 protons) ppm.

Anal. calcd. for $C_{14}H_{26}O_4$: C, 65.08; H, 10.14; Found: C, 65.10; H, 10.08.

EXAMPLE 37

A mixture of ketoketal from Example 36 (948 mg.), toluene (19 ml.) 2-methylcyclopentane-1,3-dione (620 mg.) and acetic acid (9 ml.) was heated to 115° C in an apparatus which was fitted with a Dean-Stark trap. The reaction mixture was stirred at this temperature for 15 hours. (slight reflux but not enough for distillation into the Dean-Stark trap). The temperature was then raised to 140° for 1 hour. The cooled mixture was washed with water, saturated sodium bicarbonate solution and brine. The aqueous layers were reextracted with benzene and the combined benzene extracts were washed again with brine. Drying and solvent removal afforded crude crystalline 3S,6aS,3-(4-oxo-1-pentyl)-6a-methyl-1,2,3,5,6,6a-hexahydrocyclopenta[f][1]benzopyran-7(8H)-one (1.02 g.). This material was dissolved in methanol (7 ml.) and slowly treated with water (3 ml.) over a period of 15 minutes. A first crop (421.6 mg.) was obtained, m.p. 67.5°–72° C., $[\alpha]_D^{25}$ −157.5° (C=1.01 in chloroform). The mother liquor from the crystallization was treated with more water (1.5 ml.) over a period of 1 hour. In this way a second crop (246.1 mg.) was obtained, m.p. 61°–67° C., $[\alpha]_D^{25}$ −147.7° (C=1.13 in chloroform). The first and second crops were recrystallized together from aqueous methanol to afford a pure sample (528.4 mg.; 50%); m.p. 71°–74° C; $[\alpha]_D^{25}$ −163.65° (C=0.9331 in chloroform);

ir: $\nu_{max}^{CHCl_3}$ 1740 (cyclopentanone C=O), 1710 (ketone C=O), 1640 (dienolether) cm$^{-1}$; uv: $\lambda_{max}^{EtOH}$ 254 m$\mu$($\epsilon$18600).

EXAMPLE 38

A solution of dienolether from Example 32 (5.8 g.; crude reduction product) in toluene (30 ml.) and tetrahydrofuran (20 ml. dried over aluminum oxide grade I) was hydrogenated under one atmosphere and room temperature using a 5% palladium on carbon catalyst (1.0 g., AK-4). The uptake (500 ml.) of hydrogen stopped after about 2 hours. The catalyst was filtered off and washed with THF. Solvent removal gave crude 3S,6aS,6a,9a-trans-3-(3-cyanopropyl)-6a-methyl-1,2,3,5,6,6a,7,8,9,9a-decahydrocyclopenta[f][1]benzopyran-7$\beta$-ol as an oil (5.66 g.). The ir spectrum showed absorptions 1680 cm$^{-1}$ (enolether), 2250 cm$^{-1}$ (nitrile) and 3620 cm$^{-1}$ (hydroxyl). This crude product was used for the next step.

EXAMPLE 39

A mixture of crude enolether from Example 38 (5.66 g.), acetone (110 ml.) and 1N sulfuric acid (30 ml.) was allowed to stand at room temperature for 1 hour. The reaction mixture containing 3S,6aS,6a,9a-trans-3-(3-cyanopropyl)-6a-methyl-perhydrocyclopenta[f][1]benzopyran-4a,7$\beta$-diol was then stirred and cooled to 0° and treated with freshly prepared Jones Reagent (21.5 ml.) over a period of 15 minutes. After addition, the mixture was stirred at room temperature for 3 hours. Under cooling, sodium bisulfite was added until the color of the solution turned green. The mixture was diluted with saturated brine and then extracted with benzene several times. The benzene layers were washed with saturated sodium bicarbonate and brine and then dried. Filtration and solvent removal afforded crude 6aS-trans-anti-4-(3-oxo-6-cyano-1-hexyl)3a,4,7,7a-tetrahydro-7a$\beta$-methyl-1,5(6H)-indandione as an oil. This crude product was used in the next step without purification.

EXAMPLE 40

A mixture of triketone from Example 39 (4.6 g., crude), toluene (200 ml.) and p-toluene sulfonic acid monohydrate (1.0 g.) was stirred and refluxed, under nitrogen, using a Dean-Stark trap for 4.5 hours after vigorous refluxing began. The cooled solution was washed twice with saturated sodium bicarbonate solution. The aqueous layers were back extracted with methylene chloride and the combined organic solutions were dried. Filtration and solvent removal afforded a semi-solid residue (4.0 g.). This material was triturated under ethyl acetate and the solid was suction filtered and washed with ethyl acetate. The combined filtrate and washings were concentrated and the residue (3.3 g.) chromatographed on silica gel (300 g.). Elution with benzene: ethylacetate 2:1 and 1:1 afforded 1.93 g. oil, TLC one spot. A 1.1 g. sample of this material was rechromatographed on silica gel (100 g.). Elution with benzene:ethylacetate 4:1 and 2:1 afforded (+)-trans-anti-6(2-cyanoethyl)-3a$\beta$-methyl-1,2,3,a,4,5,9,9a,9b-octahydro-3H-benz[e]inden-3,7(8H)-dione (541.9 mg., semicrystalline). This material was triturated with ether and a little benzene to afforded a pure sample (392.4 mg.) as colorless solid m.p. 111°–117° C., $[\alpha]_D^{25}$+52.5° (C=1.0 in chloroform). Recrystallization from 2-propanol afforded a pure analytical sample (308.6 mg.) m.p. 116°–119° C., $[\alpha]_D^{25}$+53.9° (C=0.9073 in chloroform).

ir: $\nu_{max}^{CHCl_3}$ 2250 (C≡N), 1740 (cyclopentanone C=O), 1665 ($\alpha,\beta$-unsaturated ketone C=O), 1605 (C=C) cm$^{-1}$; uv: $\lambda_{max}^{EtOH}$ 245 ($\epsilon$13400)m$\mu$; nmr:, $\delta_{TMS}^{CDCl_3}$ 1.04 (singlet, C$_{13}$–CH$_3$) ppm.

Anal. calcd. for $C_{17}H_{21}NO_2$: C, 75.24; H, 7.80; N, 5.16; Found: C, 74.98; H, 7.71; N, 5.00.

EXAMPLE 41

A 12.2 g. sample of triketone from Example 39 was dissolved in 40 ml. of methanol and treated with 43 ml. of a methanolic potassium hydroxide solution (0.0132 g./ml.). After heating at reflux for 45 minutes, the reaction mixture was cooled, diluted with saturated brine and the organic materials were extracted with methylene chloride. The combined organic extracts were dried, filtered and concentrated at reduced pressure. Recrystallization of the residue from 2-propanol gave 6.3 g. of pure (+)-trans-anti-6(2-cyanoethyl)-3a$\beta$-methyl-1,2,3a,4,5,9,9a,9b-octahydro-3H-benz[e]inden-3,7(8H)-dione, m.p. 115°–117°. $[\alpha]_D^{25}$+55.1° (C=1.5002; CHCl$_3$)

uv: $\lambda_{max}^{EtOH}$ 243 m$\mu$($\epsilon$14000); ir: $\nu_{max}^{CHCl_3}$ 2250 (C≡N), 1735 (cyclopentanone C=O), 1665 (cyclohexenone C=O) and 1603 (C=C) cm$^{-1}$.

Anal. calcd. for $C_{17}H_{21}NO_2$: C, 75.25; H, 7.80; N, 5.16; Found: C, 74.98; H, 7.71; N, 5.00.

EXAMPLE 42

A solution of enedione from Example 41 (230 mg.) in dry tetrahydrofuran (8 ml.) and triethylamine (0.23 ml.) was stirred in an atomsphere of hydrogen over 5% palladium on carbon (46 mg., AK-4). After 2 hours, 30 ml. of hydrogen was absorbed (19 ml. theory). The hydrogenation was stopped, the catalyst was filtered off and washed with benzene and the combined filtrate and washings concentrated to give crude, semi-crystalline product (228 mg.). This product was triturated with 2-propanol (2 ml.) to afford (+)-trans-anti-trans-anti-6-(2-cyanoethyl)-3a$\beta$-methyl-1.2,3a,4,5,5a,8,9,9a,9b-decahydrobenz[e]inden-3,7(6H)-dione (190 mg.) as a white solid, m.p. 129°–134°. An analytical specimen was obtained by recrystallization from 2-propanol, m.p. 135°–136°, $[\alpha]_D^{25}$+78.91° (C=1.0354 in CHCl$_3$); ir: $\nu_{max}^{CHCl_3}$ 2250 (C≡N), 1740 (cyclopentanone C=O), 1710 (cyclohexanone C=O) cm$^{-1}$; nmr: $\delta_{TMS}^{CDCl_3}$ 0.97 (singlet, C$_{3a}$–CH$_3$) ppm.

Anal. calcd. for $C_{17}H_{23}NO_2$: C, 74.69; H, 8.48; N, 5.12; Found: C, 74.60; H, 8.79; N, 5.13.

EXAMPLE 43

A solution of diketone from Example 42 (200 mg.), methanol (2 ml.) trimethylorthoformate (0.45 ml.) and borontrifluoride etherate (0.03 ml.) was stirred for 15 minutes at room temperature and then poured into excess saturated aqueous sodium bicarbonate solution and extracted three times with benzene. The combined benzene extracts were washed with brine and then dried. Filtration and solvent removal afforded a crude oil (242 mg.). The ir of this sample still showed absorptions at 1740 and 1720 cm$^{-1}$ (cyclopentanone and cyclohexanone; approximately 30% starting material left).

A solution of the sample above (242 mg.) in methanol (2.0 ml.), trimethylorthoformate (0.5 ml.) and 70% aqueous perchloric acid (0.02 ml.) was stirred at room temperature for 30 minutes. The reaction mixture was cooled to 0°–5° C. and treated first with triethylamine (0.03 ml.) and then with sodium bicarbonate (100 mg.). The mixture was poured into excess saturated aqueous sodium bicarbonate solution and extracted three times with benzene. The combined benzene extracts were washed with brine and then dried. Filtration and solvent removal afforded a crude oily mixture of trans-anti-trans-anti-3,3,7,7-tetramethoxy-3αβ-methyl-6-(2-cyanoethyl)perhydro-1H-benz[e]inden and an enol ether at the 6,7- or 7,8-position (241.1 mg.).

ir: $\nu_{max}^{film}$ 2840 (OCH$_3$), 2250 (C ≡ N), weak bands at 1740 (cyclopentanone C=O), 1720 (cyclohexanone C=O) and 1670 (enolether) cm$^{-1}$.

EXAMPLE 44

A solution of crude product from Example 43 (240 mg.) in anhydrous ether (15 ml.) was stirred with cooling in an ice-salt bath at −15° to 0°, while 2M ethereal methyllithium (1.5 ml., 3 mole) was quickly added from a syringe. The resulting mixture was stirred at −10° to 0° for 1.5 hours, then treated with excess saturated aqueous ammonium chloride solution. The ether layer was separated and the aqueous phase was extracted twice with ether. The combined ether solutions were washed with brine and then dried. Filtration and solvent removal afforded a mixture of trans-anti-trans-anti-3,3,7,6-tetramethoxy-3αβ-methyl-6-(3-oxo-1-butyl)perhydro-1H-benz[e]indene and the corresponding enol ether (194.8 mg.) ir: $\nu_{max}^{film}$ 2840 (OCH$_3$), 1740 and 1720 (C=O, partial hydrolysis of ketals) and 1670 (enolether) cm$^{-1}$. The absence of nitrile at 2250 cm$^{-1}$ indicated that the reaction was complete.

EXAMPLE 45

A solution of diketone from Example 42 (190.0 mg.) in dry tetrahydrofuran (5.0 ml.) was treated with ethylene glycol (0.4 ml.) trimethylorthoformate (0.4 ml.) and concentrated sulfuric acid (0.02 ml.). The resulting solution was stirred at room temperature for 1.5 hours and then treated first with triethylamine (0.04 ml.) and then with 10% aqueous sodium hydroxide solution (2.0 ml.). The resulting mixture was extracted with benzene three times. The combined benzene layers were washed with brine and then dried. Filtration and solvent removal afforded (253 mg.) of a crude solid. This material was recrystallized twice from 2-propanol to afford pure (+)-trans-anti-trans-anti-3,3,7,7-bis(ethylenedioxy)-3αβ-methyl-6-(2-cyanoethyl)perhydro-1H-benz[e]indene (169 mg.), m.p. 130°–131° C., $[\alpha]_D^{25}$+0.67° (C=1.0363 in CHCl$_3$). ir: $\nu_{max}^{CHCl_3}$ 2250 (C ≡ N) cm$^{-1}$; nmr: $\delta_{TMS}^{CDCl_3}$ 3.96, 3.86 (singlets, 8 ethylene ketal protons), 0.88 (singlet, C$_{3a}$-C$\underline{H}_3$) ppm.

Anal. calcd. for C$_{21}$H$_{31}$NO$_4$: C, 69.77; H, 8.65; N, 3.88; Found: C, 69.93; H, 8.50; N, 3.91.

EXAMPLE 46

An ethereal methyllithium solution (2.0 ml., 2M) was cooled to −15° and stirred while a solution of nitrile bis-ketal from Example 45 (176.0 mg.) in anhydrous ether (10 ml.) was added over a 5 minute period. The reaction mixture was stirred at −15° to 0° for 30 minutes and then treated at 0° with water (3.0 ml.). After dilution with brine, the ether layer was separated and the aqueous layer was extracted twice with ether. The combined ether layers were washed with brine and then dried. Filtration and solvent removal afforded the crude product (185.2 mg.) as an oil. This material was chromatographed on silica gel (18 g.) Elution with benzene:ether 2:1 and 1:1 afforded pure (−)-trans-anti-trans-anti-3,3,7,7-bis-(ethylenedioxy)3αβ-methyl-6-(3-oxo-1-butyl)perhydro-1H-benz[e]indene (151.5 mg., 82.5%) as a colorless solid, m.p. 77°–81° C., $[\alpha]_D^{25}$−6.2° (C=1.0 CHCl$_3$).

ir: $\nu_{max}^{CHCl_3}$ 1720 (ketone C=O) cm$^{-1}$.

EXAMPLE 47

A solution of the mixture from Example 44 (194 mg.) in methanol (5 ml.) and 4N aqueous hydrochloric acid solution (1.5 ml.) was stirred and refluxed for 4 hours. After cooling, the reaction mixture was diluted with brine and extracted with benzene three times. The combined benzene layers were washed with brine and then dried. Filtration and solvent removal afforded crude product (136.2 mg.). This material was chromatographed on silica gel (7.5 g.). Elution with benzene:ethylacetate 9:1 and 4:1 afforded d-(+)-19-norandrost-4-en-3,17-dione (110.1 mg.), m.p. 166°–170°, $[\alpha]_D^{25}$+131.0° (C=0.50 CHCl$_3$). Recrystallization from aqueous methanol gave a pure sample (54.7 mg.) as colorless needles, m.p. 170.5°–172°, $[\alpha]_D^{25}$+141.55° (C=1.0703 in chloroform).

ir: $\nu_{max}^{CHCl_3}$ 1740 (cyclopentanone C=O), 1665 (enone C=O), 1620 (C=C) cm$^{-1}$ uv: $\lambda_{max}^{EtOH}$ 239 m$\mu$($\epsilon$17400).

Anal. calcd. for C$_{18}$H$_{24}$O$_2$: C, 79.37; H, 8.88; Found: C, 79.41; H, 9.09.

EXAMPLE 48

A solution of keto bis-ketal from Example 46 (151.5 mg.) in methanol (4.5 ml.) and 4N aqueous hydrochloric acid solution (1.5 ml.) was stirred and refluxed for 4 hours. After cooling, the reaction mixture was diluted with brine and extracted with benzene three times. The combined benzene layers were washed with brine and then dried. Filtration and solvent removal afforded crude product (92.6 mg.) as a solid. Recrystallization from aqueous methanol gave pure d-(+)-19-norandrost-4-en-3,17-dione (57.0 mg.) as a colorless needles, m.p. 169°–172° C.; mixed m.p. with an authentic sample 169°–171° C.; $[\alpha]_D^{25}$−139.15° (C=1.0492 in chloroform);

ir: $\nu_{max}^{CHCl_3}$ 1740 (cyclopentanone C=O), 1665 (enone C=O), 1620 (C=C) cm$^{-1}$; uv: $\lambda_{max}^{EtOH}$ 240 m$\mu$($\epsilon$17720).

EXAMPLE 49

A solution of 0.5 g. (1.845 moles) of the dienol ether from Example 5 in 15 ml. of dry ether and 7 ml. of dry tetrahydrofuran was stirred with cooling at 0° while 12.5 ml. (4.61 mole equivalent) of 0.369 M ethereal methylmagnesium chloride was added dropwise over 5 minutes. The resulting slurry was stirred at 0° for 1.5 hours, then treated with 5 ml. of saturated ammonium chloride, diluted with brine and extracted three times with ether. The ether extracts were combined, washed with brine, dried, filtered and concentrated at reduced pressure giving 0.58 g. of oily 3-(3-cyanopropyl)-6a$\beta$,-7$\alpha$-dimethyl-1,2,3,5,6,6a,7,8-octahydrocyclopenta[f][1]benzopyran-7$\beta$-ol.

ir: $\nu_{max}^{film}$ 3456(OH), 2250 (C ≡ N), 1750 (trace-starting cyclopentanone), 1645 (dienolether) cm$^{-1}$. TLC analysis showed a new major spot of slower R$_f$ than the starting material as well as a trace of starting material.

The above compound may be converted to 17$\alpha$-methyl-19nortestosterone, by proceeding in a manner similar to that described in Examples 7, 8, 9, 11, 14, 15 and 17 via the intermediates 6a,9a-trans-3-(3-cyanopropyl)-6a$\beta$,7$\alpha$-dimethyl-1,2,3,5,6,6a,7,8,9,9a-decahydrocyclopenta[f][1]benzopyran-7$\beta$-ol, 6a,9a-trans-3-(3-cyanopropyl)-6a$\beta$,7$\alpha$-dimethyl-perhydrocyclopenta[f][1]benzopyran-4a,7$\beta$-diol, 3a,7a-trans-4-(3-oxo-6-cyano-1-hexyl)-3a,4,7,7a-tetrahydro-1$\alpha$,7a$\beta$-dimethyl-6H-indan-5-one, trans-anti-6-(2-cyanoethyl)-3$\alpha$,3a$\beta$-dimethyl-1,2,3,3a,4,5,8,9,9a,9b-decahydrobenz[e]inden-7-one, trans-anti-trans-anti-6-(2-cyanoethyl)-3$\alpha$,3a$\beta$-dimethyl-perhydrobenz[e]inden-3-one, trans-anti-trans-anti-7,7-ethylenedioxy-3$\alpha$,3a$\beta$-dimethyl-6-(2-cyanoethyl)perhydro-benz[e]inden-3$\beta$-ol, and trans-anti-trans-anti-7,7-ethylenedioxy-3$\alpha$,3a$\beta$-dimethyl-6-(2-cyanoethyl)-perhydrobenz[e]inden-3$\beta$-ol.

EXAMPLE 50

A stirred solution of 10 g (0.06 mole) of 8-cyano-5-hydroxyoctanoic acid lactone dissolved in 50 ml of tetrahydrofuran was cooled to −70° C in a dry ice-acetone bath and treated over 7 minutes with 33.4 ml (0.105 mole) of a solution of vinylmagnesium chloride in tetrahydrofuran (3.14 M), maintaining the reaction temperature between −50° and −0° C during the addition. The reaction mixture was then stirred at −55° C for an additional 13 minutes. Methanol (1.8 ml) was added. The dry ice-acetone was removed and 10% aqueous ammonium chloride (30 ml) and acetic acid (4.8 ml) were successively added. The layers were separated and the aqueous phase was extracted with tetrahydrofuran (2 × 20 ml). The combined organic extracts were washed with saturated sodium chloride solution. A 2 ml-aliquot was removed, dried over anhydrous sodium sulfate and filtered. Evaporation of the filtrate at 50° C under high vacuum gave 6-(3-cyanopropyl)-2-vinyltetrahydropyran-2-ol and its tautomer, the reaction product.

uv: $\pi$max (95%) ethanol) 210 nm (E 5500).

nmr: $\delta_{TMS}^{CDCl_3}$ 1.0–2.3 (multiplet, 8 protons), 2.3–32. (multiplit, 4 protons), 3.5–4.0 (multiplet, 1 proton), 5.8–6.5 ppm (multiplit, 3 protons).

We claim:

1. 6-(3-Cyanopropyl)-2-vinyl-tetrahydropyran-2-ol and its tautomer.

\* \* \* \* \*